(12) United States Patent
Lowery et al.

(10) Patent No.: US 8,323,723 B2
(45) Date of Patent: Dec. 4, 2012

(54) CONTROLLED VAPOR DEPOSITION OF BIOCOMPATIBLE COATINGS FOR MEDICAL DEVICES

(76) Inventors: Michael D Lowery, Vista, CA (US); Laurent Hoffmann, Aliso Viejo, CA (US); Boris Kobrin, Walnut Creek, CA (US); Romuald Nowak, Cupertino, CA (US); Jeffrey D Chinn, Foster City, CA (US); Richard C Yi, Santa Cruz, CA (US)

(*) Notice: Subject to any disclaimer, the term of this patent is extended or adjusted under 35 U.S.C. 154(b) by 0 days.

(21) Appl. No.: 13/107,243

(22) Filed: May 13, 2011

(65) Prior Publication Data

US 2011/0217449 A1 Sep. 8, 2011

Related U.S. Application Data

(60) Division of application No. 12/611,639, filed on Nov. 3, 2009, now Pat. No. 7,955,704, which is a continuation of application No. 11/123,487, filed on May 5, 2005, now abandoned.

(51) Int. Cl.
*A61F 2/16* (2006.01)
*C23C 16/02* (2006.01)
*B05D 3/10* (2006.01)

(52) U.S. Cl. ............... 427/2.24; 427/2.1; 427/248.1; 427/255.11; 427/255.14; 427/255.18; 623/6.11; 623/6.62

(58) Field of Classification Search .......... 427/2.1–2.31, 427/248.1, 248.15, 255.11, 255.14, 255.18, 427/2.24; 623/6.11, 6.62
See application file for complete search history.

(56) References Cited

U.S. PATENT DOCUMENTS

| | | | |
|---|---|---|---|
| 3,637,416 A * | 1/1972 | Misch et al. | 428/412 |
| 4,886,866 A * | 12/1989 | Braatz et al. | 528/59 |
| 4,976,703 A | 12/1990 | Franetzki et al. | |
| 5,002,582 A * | 3/1991 | Guire et al. | 427/2.24 |
| 5,002,794 A | 3/1991 | Ratner et al. | |
| 5,244,654 A | 9/1993 | Narayanan | |
| 5,328,768 A | 7/1994 | Goodwin | |
| 5,372,851 A | 12/1994 | Ogawa et al. | |
| 5,576,247 A | 11/1996 | Yano et al. | |
| 5,602,671 A | 2/1997 | Hornbeck | |
| 5,741,551 A | 4/1998 | Guire et al. | |
| 5,932,299 A | 8/1999 | Katoot | |
| 5,936,703 A | 8/1999 | Miyazaki et al. | |

(Continued)

FOREIGN PATENT DOCUMENTS

WO  WO0192924 A1  12/2001

(Continued)

OTHER PUBLICATIONS

Popa et al. Characterization of vapor deposited poly(ethylene)glycol films on silicon surfaces for surface modification of microfluidic systems Feb. 13, 2003.*

(Continued)

*Primary Examiner* — Timothy Meeks
*Assistant Examiner* — Cachet Sellman
(74) *Attorney, Agent, or Firm* — Abbott Medical Optics Inc.

(57) ABSTRACT

An intraocular lens with a hydrophilic polymer coating composition and method of preparing same are provided. Specifically, a composition suitable for reducing tackiness in intraocular lenses is provided wherein an acrylic intraocular lens is treated by vapor deposition with an alkoxy silyl terminated polyethylene glycol polymer composition.

3 Claims, 13 Drawing Sheets

U.S. PATENT DOCUMENTS

| | | | |
|---|---|---|---|
| 6,099,562 | A | 8/2000 | Ding et al. |
| 6,200,626 | B1 | 3/2001 | Grobe, III |
| 6,213,604 | B1 | 4/2001 | Valint, Jr. et al. |
| 6,235,340 | B1 | 5/2001 | Lee et al. |
| 6,475,808 | B1 | 11/2002 | Wagner et al. |
| 6,503,330 | B1 | 1/2003 | Sneh et al. |
| 6,509,098 | B1 | 1/2003 | Merrill et al. |
| 6,576,489 | B2 | 6/2003 | Leung et al. |
| 6,616,982 | B2 | 9/2003 | Merrill et al. |
| 7,138,471 | B2 | 11/2006 | Clayton et al. |
| 2001/0031309 | A1* | 10/2001 | Lee et al. ............. 427/2.1 |
| 2002/0064663 | A1 | 5/2002 | Murphy et al. |
| 2003/0180544 | A1 | 9/2003 | Murphy |
| 2003/0232305 | A1 | 12/2003 | Warner |
| 2004/0023413 | A1 | 2/2004 | Opalsky |
| 2004/0115591 | A1 | 6/2004 | Warner |
| 2005/0130097 | A1 | 6/2005 | Warner |
| 2005/0130098 | A1 | 6/2005 | Warner |
| 2005/0271810 | A1 | 12/2005 | Kobrin et al. |
| 2005/0271900 | A1 | 12/2005 | Kobrin et al. |
| 2006/0029732 | A1 | 2/2006 | Kobrin et al. |
| 2006/0088666 | A1 | 4/2006 | Kobrin et al. |
| 2006/0251795 | A1 | 11/2006 | Kobrin et al. |

FOREIGN PATENT DOCUMENTS

| | | |
|---|---|---|
| WO | WO03000433 A1 | 1/2003 |
| WO | WO2006121573 A1 | 11/2006 |

OTHER PUBLICATIONS

Jo et al. Surface modification using silanated poly(ethylene glycol)s. Biomaterials. vol. 21, Issue 6, Mar. 2000, pp. 605-616.*

Papra et al. Characterization of Ultrathin Poly(ethylene glycol) Monolayers on Silicon Substrates. Langmui. 2001. vol. 17.1457-1460.*

Alcantar, et al., "A Simple Efficient and Flexible Method to Create Biocompatible Surfaces—Polymeric Materials Science and Engineering," Proceedings of the ACS Division of Polymeric Materials Science and Engineering, 1997, vol. 76, pp. 619.

Alcantar N.A., et al., "Polyethylene glycol-coated biocompatible surfaces," Journal of Biomedical Materials Research, 2000, vol. 51, pp. 343-351.

Arkles B., et al., "Tailoring Surfaces with Silanes," Chemical Technology, 1977, vol. 7, pp. 766-778.

Bell D.J., et al., "Using poly(ethylene glycol) silane to prevent protein adsorption in microfabricated silicon channels," SPIE, vol. 3258, pp. 134-140.

Bubb D.M., et al., "Resonant Infrared Pulsed-Laser Deposition of Polymer Films Using a Free-Electron Laser," Journal of Vacuum Science & Technology, 2001, vol. 19 (5), pp. 2698-2702.

Bubb D.M., et al., "Vapor Deposition of Intact Polyethylene Glycol thin Films," Applied Physics, 2001, vol. 73, pp. 121-123.

Campbell A..A., et al., "Low Temperature Solution Deposition of Calcium Phosphate Coatings for Orthopedic Implants" 1994.

Ehrlich, et al., "Fast Room-Temperature Growth of $SiO_2$ Films by Molecular-Layer Dosing," Applied Physics Letters, 1991, vol. 58 (23), pp. 2675-2677.

Hoffmann Patrick et al., "Vapor Phase Self-Assembly of Fluorinated Monolayers on Silicon and Germanium Oxide," 1997, 1877-1880.

Ketul C. Popat et al., "Development of Vapor Deposited Thin Films for Biomicrosystems", 2002, 1-110.

Kim M.K., et al., "Effect of Poly (ethylene glycol) Graft Polymerization of Poly (Methyl Rnethacrylate) on Cell Adhesion," Journal of Cataract & Refractive Surgery, 2001, vol. 27, pp. 766-773.

Klaus J.W., et al., "$SiO_2$ Chemical Vapor Deposition at Room Temperature Using $SiCl_4$ and $H_2O$ with an $NH_3$ Catalyst," Journal of the Electrochemical Society, 2000, vol. 147 (7), pp. 2658-2664.

Mayer T.M., et al., "Chemical Vapor Deposition of Fluoroalkylsilane Monolayer Films for Adhesion Control in Microelectromechanical Systems," Journal of Vacuum Science & Technology, 2000, vol. 18 (5), pp. 2433-2440.

Per Mansson, "Surface-modified IOLs surface characterization using ESCA, SSIMS and inflammatory markers," Division of Polymeric Materials: Science and Engineering, pp. 1, 460, 461, 1993, American Chemical Society.

Popat K.C., et al., Vapor Deposited Polyethyleneglycol (PEG) Films for Surface Modification of Microfluidic Systems [M095], Lab Automation, 2002, Table of Contents.

Popata K.C., et al., "Characterization of Vapor Deposited Poly Ethylene Glycol Films on Silicon Surfaces for Surface Modification of Microfluidic Systems," The Journal of Vacuum Science and Technology, 2003, vol. 21 (2), pp. 645-654.

Prime K.L., et al., "Self-Assembled Organic Monolayers: Model Systems for Studying Adsorption of Proteins at Surfaces," Science, 1991, vol. 252 (5010), pp. 1164-1167.

Sagiv J., et al., "Organized Monolayers by Adsorption, I Formation and Structure of Oleophobic Mixed Monolayers on Solid Surfaces," Journal of the American Chemical Society, 1978, vol. 120 (1), pp. 92-98.

Shamamian et al., "Mass Spectrometric Characterization of Pulsed Plasmas for Deposition of Thin Polyethylene Glycol-Like Polymer Films," 2001, 341-346.

Sneh O., et al., "Atomic Layer Growth of 5102 on 51(100) Using the Sequential Deposition of SIC14 and 1120," material research society symposium, 1994, vol. 334, pp. 25-30.

Wang Jian et al., "Gold nanoparticulate film bound to silicon surface with self-assembled monolayers," 1998, 591-594.

Wang Yuchun et al., "Vapor phase deposition of uniform and ultrathin silanes," 3258, 20-28.

Zhang M., et al., "Hemocompatible Polyethylene Glycol Films on Silicon," 1998, pp. 81-89.

Zhang M., et al., "Proteins and Cells on PEG Immobilized Silicon Surfaces," Biornaterials, 1998, vol. 19, pp. 953-960.

* cited by examiner

CONTROLLED VAPOR DEPOSITION OF BIOCOMPATIBLE COATINGS FOR MEDICAL DEVICES

This application is related to and is a divisional application of U.S. patent application Ser. No. 12/611,639, filed Nov. 3, 2009, now U.S. Pat. No. 7,995,704, which is a continuation application of U.S. patent application Ser. No. 11/123,487, filed May 5, 2005, and entitled "Controlled Vapor Deposition of Biocompatible Coatings for Medical Devices", now abandoned, which is related to U.S. patent application Ser. No. 11/112,664 filed Apr. 21, 2005, and entitled "Controlled Vapor Deposition of Multilayered Coatings Adhered by all Oxide Layer", now U.S. Pat. No. 7,776,396, which is a continuation in part of U.S. patent application Ser. No. 10/996,520, filed Nov. 23, 2004, and entitled "Controlled Vapor Deposition of Multilayered Coatings Adhered by an Oxide Layer", now abandoned, which is a continuation in part of U.S. patent application Ser. No. 10/862,047, filed Jun. 04, 2004, and entitled "Controlled Deposition of Silicon-Containing Coatings Adhered by an Oxide Layer", now U.S. Pat. No. 7,638,167. This application is also related to U.S. patent application Ser. No. 11/048,513, filed Jan. 31, 2005, and entitled "High Aspect Ratio Performance Coatings for Biological Microfluidics" now U.S. Pat. No. 7,879,396, which is also a continuation in part of U.S. patent application Ser. No. 10/862,047, now U.S. Pat. No. 7,638,167, which is recited above. All of these U.S. Patents and Patent Applications are hereby incorporated by reference in their entireties.

TECHNICAL FIELD OF THE INVENTION

The present invention pertains to the surface treatment of intraocular lens (IOLs) used in medical applications which require hydrophilic, biocompatible interfaces with bodily tissues and fluids.

BACKGROUND OF THE INVENTION

In the biological field, the surface characteristics of a substrate control the functioning of that substrate relative to fluids with which the substrate surface comes in contact. Since known living organisms rely heavily on the presence of water, the hydrophilicity or hydrophobicity of a given surface plays a major role in determining whether a medical device can perform well in the environment in which it is to function. The surface of the medical device must be designed to provide biocompatibility with fluids it is to contact in the environment, and may be designed to achieve a particular interaction with the fluids it contacts. The ability of a medical device to function either in-vivo or in-vitro depends on the surface presented by the medical device. For example, with respect to an implant which is used in medical applications, the ability of the implant to integrate into the location at which it is placed and to function in combination with surrounding tissues and fluids depends significantly on the hydrophilicity or hydrophobicity of the implant surface, and frequently depends on the presence or absence on the surface of the implant of chemical compounds having particular properties. With respect to a medical device surface used for chemical analysis, for example, the device must provide a functional surface which enables the particular analytical function.

The need for biocompatible films and, in particular, for hydrophilic, neutral biocompatible surfaces that resist adhesion and growth of protein, lipids, and bacteria, drives the search for new materials compatible with medical and biological applications. For example, those skilled in the art have long recognized the need for rendering the surface of contact lenses hydrophilic in order to improve their biocompatibility or wettability by tear fluid in the eye. This is necessary to improve the wear comfort of contact lenses and/or to extend their resistance to bacterial infection, inflammation, and other adverse effects resulting from incompatibility of the lens with the human body and its functions.

In the case of contact lenses, in particular, the lens surface must be resistant to bacterial growth and infection, and must also be hydrophilic to allow for efficient binding of water by the lens and sufficient flow of oxygen to the surface of the eye. Carbohydrate type coatings are of particular interest, as they resemble the natural coating of a human cell and are less prone to inflammation and irritation of tissue due to chemical and biological incompatibility. They also have a lubricating effect caused by their high surface energy, are optically clear, and facilitate exchange of fluids between the surface of the coated device and the body.

In many applications where the wear on the coating is likely to occur due to mechanical contact or where fluid flow is to occur over the substrate surface on which the layer of coating is present, it is helpful to have the coating chemically bonded directly to the substrate surface via chemical reaction of active species which are present in the coating reactants/materials with active species on the underlying substrate surface. In addition, particular precursor materials may be selected which are known to provide particular functional moieties.

With respect to layers and coatings which are chemically bonded to a medical device surface, there are a number of areas of particular current interest. By way of example, and not by way of limitation, surface structure and exterior coatings on that surface structure may be used for biotechnology applications where the surface wetting properties and functionality are useful for analytical purposes, for controlling fluid flow and sorting of fluid components, and for altering the composition of components which come into contact with the surface, for example.

Due to the nanometer size scale of some of medical device applications which employ coatings exhibiting specialized functionality, a need has grown for improved methods of controlling the formation of the coating, including the formation of individual layers within a multi-layered coating, for example. Typically such coatings range in thickness from about 1 nm (10 Å) to about 1 micron ($\mu$). At the present time, approximately 95% of the new applications for medical device coatings make use of a coating thickness which is less than 100 nm, with a number of applications requiring a coating thickness in the range of about 50 nm to 100 nm. Historically, surface coatings for medical devices have been applied by contacting a device substrate surface with a liquid coating material. While this technique enables efficient coating deposition, it frequently results in limited control over the surface properties of the applied coating. In the case of coating a surface of a medical device which must function on a nanometer scale, use of liquid phase processing limits device yield due to contamination and capillary forces. More recently, deposition of coatings from a vapor-phase has been used in an attempt to improve coating properties. However, the common vapor-phase deposition methods may not permit sufficient control of the molecular level reactions taking place during the deposition of surface bonding layers or during the deposition of functional coatings, when the deposited coating needs to exhibit functional surface properties on a nanometer (nm) scale.

For purposes of illustrating methods of coating formation where vaporous and liquid precursors are used to deposit a coating on a substrate, applicants would like to mention the following publications and patents which relate to methods of coating formation, for purposes of illustration. Most of the background information provided is with respect to various chlorosilane-based precursors; however it is not intended that the present invention be limited to this class of precursor materials. In addition, applicants would like to make it clear that some of this Background Art is not prior art to the present invention. It is mentioned here because it is of interest to the general subject matter.

In an article by Barry Arkles entitled "Tailoring surfaces with silanes", published in CHEMTECH, in December of 1977, pages 766-777, the author describes the use of organo silanes to form coatings which impart desired functional characteristics to an underlying oxide-containing surface. In particular, the organo silane is represented as $R_nSiX_{(4-n)}$ where X is a hydrolyzable group, typically halogen, alkoxy, acyloxy, or amine. Following hydrolysis, a reactive silanol group is said to be formed which can condense with other silanol groups, for example, those on the surface of siliceous fillers, to form siloxane linkages. Stable condensation products are said to be formed with other oxides in addition to silicon oxide, such as oxides of aluminum, zirconium, tin, titanium, and nickel. The R group is said to be a nonhydrolyzable organic radical that may possess functionality that imparts desired characteristics. The article also discusses reactive tetra-substituted silanes which can be fully substituted by hydrolyzable groups and how the silicic acid which is formed from such substituted silanes readily forms polymers such as silica gel, quartz, or silicates by condensation of the silanol groups or reaction of silicate ions. Tetrachlorosilane is mentioned as being of commercial importance since it can be hydrolyzed in the vapor phase to form amorphous fumed silica.

The article by Dr. Arkles shows how a substrate with hydroxyl groups on its surface can be reacted with a condensation product of an organosilane to provide chemical bonding to the substrate surface. The reactions are generally discussed and, with the exception of the formation of amorphous fumed silica, the reactions are between a liquid precursor and a substrate having hydroxyl groups on its surface. A number of different applications and potential applications are discussed.

In an article entitled "Organized Monolayers by Adsorption. 1. Formation and Structure of Oleophobic Mixed Monolayers on Solid Surfaces", published in the Journal of the American Chemical Society, Jan. 2, 1980, pp. 92-98, Jacob Sagiv discussed the possibility of producing oleophobic monolayers containing more than one component (mixed monolayers). The article is said to show that homogeneous mixed monolayers containing components which are very different in their properties and molecular shape may be easily formed on various solid polar substrates by adsorption from organic solutions. Irreversible adsorption is said to be achieved through covalent bonding of active silane molecules to the surface of the substrate.

U.S. Pat. No. 5,002,794 to Rattier et al., issued Mar. 26, 1991, describes a method of controlling the chemical structure of polymeric films formed by plasma deposition. An important aspect of the method involves controlling the temperature of the substrate and the reactor to create a temperature differential between the substrate and reactor such that the precursor molecules are preferentially adsorbed or condensed onto the substrate either during plasma deposition or between plasma deposition steps. (Abstract) This reference discusses the immobilization of poly(ethylene glycol), also referred to as PEG or as polyethylene oxide (PEO). The application of PEG-like thin films, grafted onto a wide variety of substrates, is described as carried out using a plasma deposition apparatus. Substrates are said to be cleaned by etching with an argon plasma in some instances. An object to be treated is placed in a vacuum chamber, and reactant precursor is introduced into the chamber at a specified rate so as to maintain a constant pressure in the reactor. A power supply is used to maintain a plasma at a set power level during the deposition. The disclosure teaches that, depending on the length of time the plasma is maintained, the thickness of the deposited films may be controlled as desired. The precursor material is introduced into the reaction vessel and pressure and flow of the precursor material are stabilized, with the plasma deposition and condensation carried out simultaneously or alternately for any desired length of time. After the deposition is complete, the coated specimens may be permitted to remain in the presence of the precursor "to permit the chemical reactions in the film to go to completion". This is referred to as a quench step. The disclosure of this reference is hereby incorporated by reference in its entirety.

Kevin L. Prime et al. published an article entitled "Self-Assembled Organic Monolayers: Model Systems for Studying Adsorption of Proteins at Surfaces" in Science 1991, 252, pp. 1164-1167. Self-assembled monolayers (SAMS) of ω-functionalized long-chain alkanethiolates on gold films are described as excellent model systems with which to study the interactions of proteins with organic surfaces. Monolayers containing mixtures of hydrophobic (methyl terminated) and hydrophilic [hydroxyl-, maltose-, and hexa(ethylene glycol)-terminated] alkanethiols are said to be tailored to select specific degrees of adsorption. The SAMS were prepared by the chemisorption of alkanethiols from 0.25 mM solutions in ethanol or methanol onto thin (200.+−0.20 nm) gold films supported on silicon wafers. The hexa(ethylene glycol)-terminated SAMS are said to be the most effective in resisting protein adsorption. (Abstract) The subject matter of this article is hereby incorporated by reference in its entirety.

In June of 1991, D. J. Ehrlich and J. Melngailis published an article entitled "Fast room-temperature growth of $SiO_2$ films by molecular-layer dosing" in Applied Physics Letters 58 (23), pp. 2675-2677. The authors describe a dosing technique for room-temperature growth of .alpha.-$SiO_2$ thin films, which growth is based on the reaction of $H_2O$ and $SiCl_4$ adsorbates. The reaction is catalyzed by the hydrated $SiO_2$ growth surface, and requires a specific surface phase of hydrogen-bonded water. Thicknesses of the films is said to be controlled to molecular-layer precision; alternatively, fast conformal growth to rates exceeding 100 nm/min is said to be achieved by slight depression of the substrate temperature below room temperature. Potential applications such as trench filling for integrated circuits and hermetic ultrathin layers for multilayer photoresists are mentioned. Excimer-laser-induced surface modification is said to permit projection-patterned selective-area growth on silicon.

An article entitled "Atomic Layer Growth of $SiO_2$ on Si(100) Using The Sequential Deposition of $SiCl_4$ and $H_2O$" by Sneh et al. in Mat. Res. Soc. Symp. Proc. Vol 334, 1994, pp. 25-30, describes a study in which $SiO_2$ thin films were said to be deposited on Si(100) with atomic layer control at 600° K ($\cong$327° C.) and at pressures in the range of 1 to 50 Torr using chemical vapor deposition (CVD).

A. A. Campbell et al. presented a paper "Low Temperature Solution Deposition of Calcium Phosphate Coatings For Orthopedic Implants" at the American Ceramic Society Meeting, Apr. 24-28, 1994, in Indianapolis, Ind., published by NTiS, document DE94014497, which describes the growth of calcium phosphate coatings from aqueous solution onto a derivatized self-assembled monolayer (SAM) which was covalently bound to a titanium metal substrate. The SAM molecules were reported as providing an [ideal] connection between the metal surface and the calcium phosphate coating. A trichlorosilane terminus of the SAM molecule was reported as insuring covalent attachment to the substrate, while a fractionalized "tail" of the SAM molecule induced heterogeneous nucleation of the calcium phosphate coating from supersaturated solutions. (Abstract) The introduction of the article explains that bone and dental implant technology is currently inadequate. The bond between bone and implant materials (such as Ti and metal alloys) is said to fail, requiring additional surgery to remove and replace the implant after only a few years of use. To date, hydroxyapatite (HAP) coatings are said to have shown exceptional promise as bioactive coatings for metallic implant devices. It is commented that the apatite may be able to partially dissolve, intergrow, and become partially incorporated with the apatite in growing bone, forming a coating: bone interface as strong as the bone itself. The subject matter of this reference is hereby incorporated by reference in its entirety.

U.S. Pat. No. 5,328,768 to Goodwin, issued Jul. 12, 1994, discloses a method and article wherein a glass substrate is provided with a more durable non-wetting surface by treatment with a perfluoroalkyl alkyl silane and a fluorinated olefin telomer on a surface which comprises a silica primer layer. The silica primer layer is said to be preferably pyrolytically deposited, magnetron sputtered, or applied by a sol-gel condensation reaction (i.e. from alkyl silicates or chlorosilanes). A perfluoroalkyl alkyl silane combined with a fluorinated olefin telomer is said to produce a preferred surface treatment composition. The silane/olefin composition is employed as a solution, preferably in a fluorinated solvent. The solution is applied to a substrate surface by any conventional technique such as dipping, flowing, wiping, or spraying.

In U.S. Pat. No. 5,372,851, issued to Ogawa et al. on Dec. 13, 1995, a method of manufacturing a chemically adsorbed film is described. In particular a chemically adsorbed film is said to be formed on any type of substrate in a short time by chemically adsorbing a chlorosilane based surface active-agent in a gas phase on the surface of a substrate having active hydrogen groups. The basic reaction by which a chlorosilane is attached to a surface with hydroxyl groups present on the surface is basically the same as described in other articles discussed above. In a preferred embodiment, a chlorosilane based adsorbent or an alkoxyl-silane based adsorbent is used as the silane-based surface adsorbent, where the silane-based adsorbent has a reactive silyl group at one end and a condensation reaction is initiated in the gas phase atmosphere. A dehydrochlorination reaction or a de-alcohol reaction is carried out as the condensation reaction. After the dehydrochlorination reaction, the unreacted chlorosilane-based adsorbent on the surface of the substrate is washed with a non-aqueous solution and then the adsorbed material is reacted with aqueous solution to form a monomolecular adsorbed film.

Patrick W. Hoffmann et al., in an article published by the American Chemical Society, Langmuir 1997, 13, pp. 1877-1880, entitled: "Vapor Phase Self-Assembly of Fluorinated Monolayers on Silicon and Germanium Oxide" describe the surface coverage and molecular orientation of monomolecular thin organic films on a Ge/Si oxide substrate. A gas phase reactor was said to have been used to provide precise control of surface hydration and reaction temperatures during the deposition of monofunctional perfluorated alkylsilanes. Complete processing conditions are not provided, and there is no description of the apparatus which was used to apply the thin films.

Miqin Zhang et al., in an article entitled "Hemocompatible Polyethylene Glycol Films on silicon", published in Biomedical Microdevices, 1(1), pp. 81-87 (1998), describe the functionalization of polyethylene glycol (PEG) by $SiCl_3$ groups on its chain ends, and the reaction of the PEG organosilicon derivatives with hydroxylated groups on silicon surfaces. The reactant preparations and the attachment of PEG film onto silicon surfaces were carried out in a glass apparatus which prevented exposure to the atmosphere. Nitrogen was used as the isolation gas, and the precursor formation reactions were carried out in solutions, with attachment of the precursor to the silicon surface by contact of a precursor solution with the silicon surface.

In another article entitled "Proteins and cells on PEG immobilized silicon surfaces", published in Biomaterials 19 (1998) pp. 953-960, Zhang et al. describe the modification of silicon surfaces by covalent attachment of self-assembled polyethylene glycol (PEG) film. Adsorption of albumin, fibrinogen, and IgG to PEG immobilized silicon surfaces was studied to evaluate the non-fouling and non-immunogenic properties of the surfaces. The adhesion and proliferation of human fibroblast and Hela cells onto the modified surfaces were investigated to examine their tissue biocompatibility. Coated PEG chains were said to show the effective depression of both plasma protein adsorption and cell attachment to the modified surfaces. The mechanisms accounting for the reduction of protein adsorption and cell adhesion on modified surfaces were discussed. (Abstract) This article is hereby incorporated by reference in its entirety, PEG was immobilized on silicon by the functionalization of a PEG precursor in the manner described in the article discussed above.

In an article entitled "Vapor phase deposition of uniform and ultrathin silanes" by Yuchun Wang et al, SPIE Vol. 3258-0277-786X/98 pp. 20-38, the authors discuss the need for ultrathin coatings on the surfaces of biomedical microdevices to regulate hydrophilicity and to minimize unspecific protein adsorption. It is recommended that silane "monolayers" which are typically formed on surfaces in organic solution, be vapor deposited instead, to reduce the formation of variable thickness films and the formation of submicron aggregates or islands on the silicon substrate surface. The vapor phase coating method is carried out at ambient pressure using nitrogen to flush out the system, and subsequently using nitrogen as a carrier gas for the reactants. (Abstract) It is mentioned that an alternative strategy consists of (applying) coating silanes in high vacuum, but no process conditions were provided. Biomedical devices formed by the method are said to be useful in the formation of microfabricated filters which regulate hydrophilicity of a surface and minimize unspecific protein absorption.

Darrel J. Bell et al., in an article entitled "Using polyethylene glycol) silane to prevent protein adsorption in microfabricated silicon channels", SPIE Vol. 3258-0277-786X/98, pp. 134-140, describe progress toward achieving a long-term antifouling surface for use in chemical and biological agent purification and detection. Poly(ethylene glycol) (PEG) silane is covalently bonded to the hydroxyls of an oxide layer on a silicon device surface and the Pyrex cover slip. (Abstract) Patterned silicon wafers are thermally oxidized to provide an oxide layer for silanization chemistry. (Page 135) A PEG-3400 silane was dissolved in anhydrous toluene to form either a 1% or a 2% solution. Silicon and Pyrex samples were placed in stirred PRG solution for varying times (24, 4 and 1.5 hours) to deposit a layer of PEG. Subsequently, all samples underwent 2-5 minute sonicating rinses in fresh anhydrous toluene before being cured for 14 hours at a temperature of 125° C. in a vacuum under 30 in. Hg.

In an article entitled "$SiO_2$ Chemical Vapor Deposition at Room Temperature Using $SiCl_4$ and $H_2O$ with an $NH_3$ Catalyst", by J. W. Klaus and S. M. George in the Journal of the Electrochemical Society, 147 (7) 2658-2664, 2000, the authors describe the deposition of silicon dioxide films at room temperature using a catalyzed chemical vapor deposition reaction. The $NH_3$ (ammonia) catalyst is said to lower the required temperature for $SiO_2$ CVD from greater than 900° K to about 313-333° K.

U.S. Patent Publication No. US 2002/0065663 A1, published on May 30, 2002, and titled "Highly Durable Hydrophobic Coatings And Methods", describes substrates which have a hydrophobic surface coating comprised of the reaction products of a chlorosilyl group containing compound and an alkylsilane. The substrate over which the coating is applied is preferably glass. In one embodiment, a silicon oxide anchor layer or hybrid organo-silicon oxide anchor layer is formed from a humidified reaction product of silicon tetrachloride or trichloromethylsilane vapors at atmospheric pressure. Application of the oxide anchor layer is followed by the vapor-deposition of a chloroalkylsilane. The silicon oxide anchor layer is said to advantageously have a root mean square surface (RMS) roughness of less than about 6.0 nm, preferably less than about 5.0 nm and a low haze value of less than about 3.0%. The RMS surface roughness of the silicon oxide layer is preferably said to be greater than about 4 nm, to improve adhesion. Too small an RMS surface is said to result in the surface being too smooth, that is to say an insufficient increase in the surface area/or insufficient depth of the surface peaks and valleys on the surface. However, too great an RMS surface area is said to result in large surface peaks, widely spaced apart, which begins to diminish the desirable surface area for subsequent reaction with the chloroalkylsilane by vapor deposition.

Simultaneous vapor deposition of silicon tetrachloride and dimethyldichlorosilane onto a glass substrate is said to result in a hydrophobic coating comprised of cross-linked polydimethylsiloxane which may then be capped with a fluoroalkylsilane (to provide hydrophobicity). The substrate is said to be glass or a silicon oxide anchor layer deposited on a surface prior to deposition of the cross-linked polydimethylsiloxane. The substrates are cleaned thoroughly and rinsed prior to being placed in the reaction chamber.

U.S. Pat. No. 5,936,703 to Miyazaki et al, issued Aug. 10, 1999 describes a specialized alkoxysilane compound or its acid-processed reaction product, which is used as a surface processing solution for a contact lense surface. The compound is said to be capable of providing hydrophilicity to the surface of various substrates which are treated with a surface processing solution of the compound. The hydrophilicity is said to be peculiar to the specialized alkoxysilane compound, whereas other silane coupling agents containing alkoxysilane groups are said to have been used to provide hydrophobic properties to the surface of inorganic or organic materials. (Abstract and Col. 1, lines 31-38.)

T. M. Mayer et al. describe a "Chemical vapor deposition of fluoroalkylsilane monolayer films for adhesion control in micro electromechanical systems" in J. Vac. Sci. Technol. B 18(5), September/October 2000. This article mentions the use of a remotely generated microwave plasma for cleaning a silicon substrate surface prior to film deposition, where the plasma source gas is either water vapor or oxygen.

U.S. Pat. No. 6,200,626 to Grobe, III et al., issued Mar. 13, 2001, describes an optically clear, hydrophilic coating produced on the surface of a silicone medical device by sequentially subjecting the surface of a lens to plasma polymerization reaction in a hydrocarbon atmosphere, to produce a carbon layer, then graft polymerizing a mixture of monomers comprising hydrophilic monomers onto the carbon layer. The invention is said to be especially useful for forming a biocompatible coating on silicone hydrogen contact lenses. (Abstract) The invention is said to be directed toward treatment of silicone medical devices. (Col. 3, lines 17-19.) Various silicon-containing monomers and a silicone hydrogel material are described, which may be used to provide a substrate. (Col. 3-Col. 6.)

Typically, the substrate surface is plasma oxidized, using a strong oxidizing plasma (Col. 8, lines 11-19), followed by plasma-polymerization deposition with a C1 to C10 saturated or unsaturated hydrocarbon to form a polymeric carbonaceous primary coating, followed by a grafting of a mixture of monomers (inclusive of macromers) onto the carbonaceous primary coating, to form a hydrophilic, biocompatible secondary coating. (Col. 7, lines 40-49.) The grafting reaction may employ an initiator, or the carbonaceous layer may be activated to promote the covalent attachment of polymer to the surface. The grafting polymer may be formed by using an aqueous solution of an ethylenically unsaturated monomer or a mixture of monomers capable of undergoing graft addition polymerization. (Col. 9, lines 18-53.)

U.S. Pat. No. 6,213,604 to Valint, Jr. et al., issued Apr. 10, 2001, describes plasma surface treatment of silicone hydrogel contact lenses. In particular, the surface of a contact lens is modified to increase its hydrophilicity by coating the lens with a carbon-containing layer made from a diolefinic compound having 4 to 8 carbon atoms. In one embodiment, an optically clear, hydrophilic coating is provided upon the surface of a silicone hydrogel lens by sequentially subjecting the surface of the lens to: a plasma oxidation reaction, followed by a plasma polymerization reaction in the presence of a diolefin, in the absence of air (in the absence of oxygen or nitrogen, where "absence" is defined to mean at a concentration of less than 10% by weight of oxygen or nitrogen, preferably less than two percent, and most preferably zero percent). Finally, the resulting carbon-containing layer is rendered hydrophilic by a further plasma oxidation reaction or by the attachment of a hydrophilic polymer chain. (Abstract and Col. 2, lines 44-53). Silicone lenses which are hydrogels can absorb and retain water in an equilibrium state. Hydrogels generally have a water content greater than about five weight percent and more commonly between about ten to about eighty weight percent. (Col. 1, lines 19-27.)

D. M. Bubb et al., in an article entitled "Vapor deposition of intact polyethylene glycol thin films", published in Appl. Phys. A (2001) Digital Object Identified (DOI) 10.1007/s003390100884, describe the deposition of polyethylene glycol (PEG) films of average molecular weight, 1400 amu, by both matrix assisted pulsed laser evaporation (MAPLE) and pulsed laser deposition (PLD). Films were deposited on NaCl plates, Si(111) wafers, and glass slides. The MAPLE deposited films are said to have shown nearly identical resemblance to the starting material, while the PLD films did not. (Abstract) In MAPLE, the material to be deposited is dissolved in an appropriate solvent, typically at 0.1 to 2.0 wt. % concentration and is frozen solid. The composite is evaporated using a pulsed laser. The vaporized solvent is said not to form a film, and is pumped away by the vacuum system in the film deposition chamber.

V. A. Shamamian et al., in an article entitled "Mass Spectrometric Characterization of Pulsed Plasmas for Deposition of Thin Polyethylene Glycol-Like Polymer Films", published in 2001 by the Society of Vacuum Coaters 505/856-7188, 44th Annual Technical Conference Proceedings, Philadelphia, Apr. 21-26, 2001, describe the characterization of pulsed inductively coupled rf plasmas of two organic precursor molecules, isopropyl alcohol and 1,4 dioxane using Langmuir probes and in situ mass spectrometry. The ultimate goal of the work was to develop predictable models for PECVD processes for thin polymer films with functionalized surfaces. (Abstract) Polyethylene glycol, or PEG-like structures were chosen as the target PECVD functional groups. The precursors mentioned above are precursors for a cyclic version of a diethylene glycol structure.

Daniel M. Bubb et al., in an article entitled "Resonant infrared pulsed-laser deposition of polymer films using a free-electron laser", published in J. Vac. Sci. Technol. A 19(5), September/October 2001, pp. 2698-2702, describe the pulsed laser deposition (PLD) of thin films of polyethylene glycol (MW 1500) using both a tunable infrared ($\lambda$=2.9 pan, 3.4 µm) and ultraviolet laser ($\lambda$ 193 nm). When the IR laser is tuned to a resonant absorption in the polymer, the IR PLD thin films are said to be identical to the starting material, where the UV PLD are said to show significant structural modification. (Abstract)

U.S. Pat. No. 6,475,808 to Wagner et al., issued Nov. 5, 2002, describes arrays of proteins which are used for in vitro screening of biomolecular activity. Methods of using the protein arrays are also disclosed. The protein arrays are said to be immobilized on one or more organic thin films on a substrate surface. (Abstract) A number of different methods for immobilizing the proteins are discussed. One of the methods described is the use of a self-assembled monolayer having an end group X available which provides chemisorption or physisorption of the monolayer onto the surface of a substrate. If the substrate is a material such as silicon, silicon oxide, or a metal oxide, then X may be a monohalosilane, dihalosilane, trihalosilane, trialkoxysilane, dialkoxysilane, or a monoalkoxysilane. (Col. 15, lines 31-51) The other end group of the self-assembled monolayer, Y, provides coupling with the protein readily under normal physiological conditions not detrimental to the activity of the protein. The functional group Y may either form a covalent linkage or a noncovalent linkage with the protein. (Col. 16, lines 33-49.) Particular deposition techniques for application of the self-assembled monolayer are not disclosed.

Ketul C. Popat et al., in an article entitled "Characterization of vapor deposited polyethylene glycol) films on silicon surfaces for surface modification of microfluidic systems", in the J. Vac. Sci. Technol. B 21(2), March/April 2003 at pages 645-654, discuss microfluidic systems which employ Poly (ethylene glycol) (PEG) as a surface coating to reduce protein adsorption on microfluidic surfaces. The PEG is said to reduce protein adsorption on the microfluidic surface. The authors developed a method of vapor deposition for the PEG which is said to be helpful when the size of microfluidic surfaces is in the micro/nanoscale range. Films deposited using the vapor deposition technique are said to decrease protein adsorption by 80% and to be stable for a period of 4 weeks. (Abstract).

The authors describe the use of silanes as precursors or bridges to connect a PEG molecule to a surface. The silane precursors are described as highly sensitive to moisture, forming aggregates and lumps on a silicon surface in the presence of moisture. These aggregates are said to clog or mask micro/nano-size features on devices. The article focuses on the vapor deposition of silane and, subsequently, PEG on silicon surfaces in a moisture free nitrogen atmosphere. To deposit PEG on a surface, a basic starting molecule of ethylene oxide is used in combination with a gas catalyst. (Page 646) A substrate surface was a silicon wafer, p-type, boron doped, with (1,0,0) orientation. The silicon surface was treated with ammonium hydroxide and hydrogen peroxide in distilled water to attach an —OH group to the surface. Ethylene oxide in vapor phase was used to grow PEG on the silicon surface. The surface was first silanized with a reactive end group silane like 3-APTMS. This is a bifunctional organosilane possessing a reactive primary amine and a hydrolyzable inorganic trimethoxysilyl group. This is a short-chained silane with a boiling point of 194° C. It is said to violently react with water and to tend to polymerize on surfaces forming lumps and aggregates. Therefore the application of the silane to the silicon surface is said to be carried out in a moisture free environment to reduce the risk of formation of lumps and aggregates on the substrate surface. (Page 647)

Boron trifluoride was used as a gaseous catalyst in combination with the ethylene oxide during formation of the PEG on the silicon surface. The boron trifluoride is said to be a weak Lewis acid which accepts a free pair of electrons of —NH$_2$ on APTMS, to make a reaction site available for a reactive ethylene oxide molecule to attach and then an additional polymerization reaction to form PEG on the substrate surface. The PEG composition is said to be controlled by the concentration of ethylene oxide and the polymerization time. The reaction is said to be terminated by flowing inert gas over the surface after an appropriate time. Nitrogen gas is used at specific flow rates through the PEG deposition chamber to maintain an inert atmosphere in the chamber. Silane is injected "in the flow loop" which is heated and maintained at a temperature a little above the boiling point of silane. Vapors of the silane are picked up by the running nitrogen. This is said to facilitate the reaction on the silicon surface to form a thin organosilane film. Nitrogen is flowed through the deposition chamber to remove unreacted silane. Ethylene oxide and boron trifluoride at a ratio of 1:2 were maintained in the reaction chamber during deposition of the PEG film. (Page 647) The disclosure of this article is hereby incorporated by reference in its entirety. More details of this work are presented in a Doctor of Philosophy graduate thesis titled: "Development Of Vapor Deposited Thin Films For Bio-Microsystems" by Ketul C. Popat, approved at the University of Illinois at Chicago on Oct. 11, 2002, the content of which is hereby incorporated by reference in its entirety.

U.S. Pat. No. 6,576,489 to Leung et al., issued Jun. 10, 2003, describes methods of forming microstructure devices. The methods include the use of vapor-phase alkylsilane-containing molecules to form a coating over a substrate surface. The alkylsilane-containing molecules are introduced into a reaction chamber containing the substrate by bubbling an anhydrous, inert gas through a liquid source of the alkylsilane-containing molecules, and transporting the molecules with the carrier gas into the reaction chamber. The formation of the coating is carried out on a substrate surface at a temperature ranging between about 15° C. and 100° C., at a pressure in the reaction chamber which is said to be below atmospheric pressure, and yet sufficiently high for a suitable amount of alkylsilane-containing molecules to be present for expeditious formation of the coating.

U.S. Patent Publication No. 2003/0180544 A1, published Sep. 25, 2003, and entitled "anti-Reflective Hydrophobic Coatings and Methods, describes substrates having anti-reflective hydrophobic surface coatings. The coatings are typically deposited on a glass substrate. A silicon oxide anchor layer is formed from a humidified reaction product of silicon tetrachloride, followed by the vapor deposition of a chloroalkylsilane. The thickness of the anchor layer and the over-layer are said to be such that the coating exhibits light reflectance of less than about 1.5%. The coatings are said to be comprised of the reaction products of a vapor-deposited chlorosilyl group containing compound and a vapor-deposited alkylsilane.

U.S. Patent Publication No. US2004/0023413 A1, of Cindra Opalsky, published Feb. 5, 2004, describes the use of polyethylene glycol, or a block co-polymer and/or derivative thereof which has been immobilized on a planar oxide surface that has been silanized. The immobilized molecule is then used in a microscale screening or binding assay in an optimal hydrogel environment (Abstract). The polyethylene glycol is typically used in the form of a "hydrogel", where the term hydrogel refers to a gelatinous colloid or aggregate of molecules in a finely dispersed semi-liquid state, where the molecules are in the external or dispersion phase and water is in the internal or dispersed phase. Preferred hydrogels are made using polyethylene glycol, polypropylene glycol or polysine, or a derivative (such as a branched or star molecule) or block co-polymer thereof. The immobilization or coupling of a hydrogel to a surface is typically carried out by contacting the hydrogel with a surface of interest to cause a physical or chemical reaction to occur between the hydrogel and the surface via one or more linkers. For chemical attachment of the hydrogel to the surface, preferred surfaces include compositions containing oxides of silicon or tungsten. In addition, a silanized planar surface is also mentioned, where a surface having hydroxyl groups present is reacted with an organosilane compound to create additional reactive groups for chemical coupling. Preferably, one or more linkers comprising the hydrogel are contacted with the surface by depositing an aqueous solution directly onto the surface, which optionally may contain an intermediate layer to facilitate binding. This reference is hereby incorporated by reference in its entirety.

Other known related references pertaining to coatings deposited on a substrate surface from a vapor include the following, as examples and not by way of limitation. U.S. Pat. No. 5,576,247 to Yano et al., issued Nov. 19, 1996, entitled: "Thin layer forming method where hydrophobic molecular layers preventing a BPSG layer from absorbing moisture". U.S. Pat. No. 5,602,671 of Hornbeck, issued Feb. 11, 1997, which describes low surface energy passivation layers for use in micromechanical devices. Jian Wang et al., in an article published in Thin Solid Films 327-329 (1998) 591-594, entitled: "Gold nanoparticulate film bound to silicon surface with self-assembled monolayers", discuss a method for attaching gold nanoparticles to silicon surfaces with a self aligned monolayer (SAM) used for surface preparation".

Other known related references pertaining to coatings deposited on a substrate surface from a vapor include the following, as examples and not by way of limitation. U.S. Pat. No. 5,576,247 to Yano et al., issued Nov. 19, 1996, entitled: "Thin layer forming method where hydrophobic molecular layers preventing a BPSG layer from absorbing moisture". U.S. Pat. No. 5,602,671 of Hornbeck, issued Feb. 11, 1997, which describes low surface energy passivation layers for use in micromechanical devices.

Some of the various methods useful in applying layers and coatings to a substrate have been described above. There are numerous other patents and publications which relate to the deposition of functional coatings on substrates, but which appear to us to be more distantly related to the present invention. However, upon reading these informative descriptions, it becomes readily apparent that control of coating deposition on a molecular level is not addressed in adequate detail in most instances. When this is discussed, the process is typically described in generalized terms like those mentioned directly above, which terms are not enabling to one skilled in the art, but merely suggest experimentation. To provide a monolayer or a few layers of a functional coating on a substrate surface which is functional or exhibits features on a nanometer scale, it is necessary to tailor the coating precisely. Without precise control of the deposition process, the coating may lack thickness uniformity and surface coverage, providing a rough surface. Or, the coating may vary in chemical composition across the surface of the substrate. Or, the coating may differ in structural composition across the surface of the substrate. Any one of these non-uniformities may result in functional discontinuities and defects on the coated substrate surface which are unacceptable for the intended application of the coated substrate.

U.S. patent application Ser. No. 10/759,857 of the present applicants describes processing apparatus which can provide specifically controlled, accurate delivery of precise quantities of reactants to the process chamber, as a means of improving control over a coating deposition process. The subject matter of the '857 application is hereby incorporated by reference in its entirety. The focus of the present application is the control of process conditions in the reaction chamber in a manner which, in combination with delivery of accurate quantities of reactive materials, provides a uniform, functional coating on a nanometer scale. The coating exhibits sufficient uniformity of thickness, chemical composition and structural composition over the substrate surface that such nanometer scale functionality is achieved.

SUMMARY OF THE INVENTION

The present invention provides IOLs with coatings suitable for reducing tackiness in the lens and methods for providing IOLs with the coatings. More specifically, the present invention provides coated IOLs comprising an acrylic polymer substrate and a polyethylene glycol coating material for making the IOL less tacky and thereby reducing the risk of damage to the lens either before or during insertion.

According to an embodiment of the present invention, an intraocular lens is provided having a coating comprising a polyethylene glycol polymer having a plurality of monomers of the structure of Formula 1:

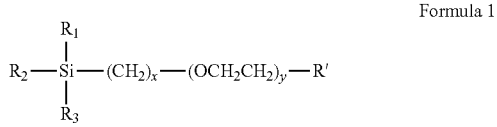

Formula 1 wherein $R_1$, $R_2$ and $R_3$ can be, individually a chlorine or a methoxy group; x is 3; y is an integer from 6 to 9; and R' is a methoxy.

According to an embodiment, the coating is vapor deposited by the method comprising the steps of a) exposing a surface of the intraocular lens to an oxygen-comprising plasma in a processing chamber which is at subatmospheric pressure; b) subsequently, without exposure of said oxygen-comprising plasma treated surface to ambient conditions which contaminate or react with said plasma treated surface, exposing said surface to a silicon chloride containing vapor in the presence of moisture, to form a hydrophilic silicon oxide layer on said surface; and c) subsequently, without exposure of said hydrophilic silicon oxide layer to ambient conditions which contaminate or react with said hydrophilic silicon oxide layer, exposing said silicon oxide layer to the polyethylene glycol polymer having a plurality of monomers of the structure of Formula 1 to form a layer selected from the group consisting of a monolayer, a self-aligned monolayer, and a polymerized cross-linked layer. In an embodiment the method may further comprise the steps of d) repeating steps a) through c), or repeating step b) through c), or repeating step c) a nominal number of times, without exposing said substrate to ambient conditions.

In an another embodiment, the coating is vapor deposited by the method comprising the steps of: a) exposing a surface of the intraocular lens to a silicon chloride containing vapor in the presence of moisture, to form a hydrophilic SixOy layer on the surface; and b) subsequently, without exposure of said hydrophilic silicon oxide layer to ambient conditions which contaminate or react with said SixOy layer, exposing said SixOy layer to the polyethylene glycol polymer having a plurality of monomers of the structure of Formula 1 to form a layer selected from the group consisting of a monolayer, a self-aligned monolayer, and a polymerized cross-linked layer. In another embodiment the method may further comprise the steps of: e) repeating steps a) through b), or repeating step b) a nominal number of times, without exposing said substrate to ambient conditions. Additionally, in an embodiment R1, R2 and R3 all may comprise methoxy groups.

According to another embodiment of the present invention, an IOL is provided having a coating comprising a polyethylene glycol polymer having a plurality of monomers wherein the monomer has the structure of Formula 2:

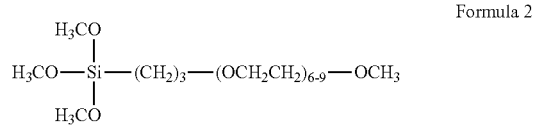

Formula 2

According to an embodiment of the present invention, a method for providing an intraocular lens surface with a hydrophilic polymer coating is also provided comprising applying at least one hydrophilic polymer coating to at least one surface of said intraocular lens using vapor deposition.

In an embodiment, the vapor deposition may comprise the steps of: a) exposing a surface of the intraocular lens to an oxygen-comprising plasma in a processing chamber which is at subatmospheric pressure; b) subsequently, without exposure of said oxygen-comprising plasma treated surface to ambient conditions which contaminate or react with said plasma treated surface, exposing said surface to a silicon chloride containing vapor in the presence of moisture, to form a hydrophilic silicon oxide layer on said surface; and c) subsequently, without exposure of said hydrophilic silicon oxide layer to ambient conditions which contaminate or react with said hydrophilic silicon oxide layer, exposing said silicon oxide layer to the polyethylene glycol polymer having a plurality of monomers of the structure of Formula 1 to form a layer selected from the group consisting of a monolayer, a self-aligned monolayer, and a polymerized cross-linked layer.

According to an embodiment, the at least one hydrophilic polymer coating may be comprised of monomers having the structure of Formula 1:

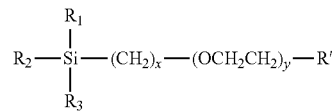

Formula 1 wherein $R_1$, $R_2$ and $R_3$ can be, individually a chlorine or a methoxy group; x is 3; y is an integer from 6 to 9; and R' is a methoxy. In an embodiment, $R_1$, $R_2$ and $R_3$ may all comprise methoxy groups. In another embodiment, the monomer may have the structure of Formula 2:

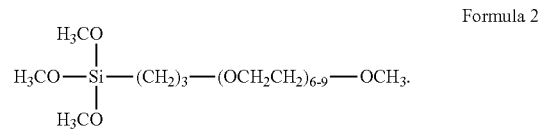

Formula 2

BRIEF DESCRIPTION OF THE DRAWINGS

The present invention is best understood with reference to the following detailed description of the invention and the drawings in which:

FIG. 3A shows the schematic for an AFM picture of a 4 nm thick silicon oxide bonding layer deposited from $SiCl_4$ precursor using the method of the present invention, where the RMS roughness is about 1.4 nm;

FIG. 3B shows the schematic for an AFM picture of a 30 nm thick silicon oxide bonding layer deposited from $SiCl_4$ precursor using the method of the present invention, where the RMS roughness is about 4.2 nm;

FIG. 10A shows data for a silicon substrate surface;

In FIG. 11A, the hydrophobic polymeric surface of the polystyrene substrate does not permit a sample drop to enter the well.

DETAILED DESCRIPTION OF THE INVENTION

Reference will now be made in detail to embodiments of the invention, examples of which are illustrated in the accompanying drawings. While the invention will be described in conjunction with the embodiments, it will be understood that they are not intended to limit the invention to those embodiments. On the contrary, the invention is intended to cover alternatives, modifications, and equivalents, which may be included within the spirit and scope of the invention as defined by the appended claims.

As a preface to the detailed description, it should be noted that, as used in this specification and the appended claims, the singular forms "a", "an", and "the" include plural referents, unless the context clearly dictates otherwise.

The use of "about" herein is intended to show that the value referred to is not an absolute limit, and may be within about ±10 percent of the nominal value recited.

As a basis for understanding the invention, it is necessary to discuss a processing apparatus which permits precise control over the addition of coating precursors and other vaporous components present within the reaction/processing chamber in which the coating is applied. The apparatus described below is not the only apparatus in which the present invention may be practiced; it is merely an example of one apparatus which may be used. One skilled in the art will recognize equivalent elements in other forms which may be substituted and still provide an acceptable processing system.

Disclosed herein is a method of increasing the hydrophilicity of a biomedical device, where a surface of the device is vapor deposition coated with a material having a hydrophilicity which is related to the surface tension of a biological fluid which is present in or around the device. Fluids which are present in or around the implant or device are typically hydrophilic (typically, water-based fluids), and a surface of the device is coated with a coating which increases the hydrophilicity of the device surface. The most common vapor-deposited coating used to increase hydrophilicity includes at least one oxide-based layer and at least one organic functional layer, where an organic functional layer provides the upper surface of the coating. When the organic functional layer is a PEG-based layer, the vapor deposited coating typically exhibits a deionized water wetting angle ranging from about 5° or less to about 60°; more typically, ranging from about 9° or less to about 50°; most typically, ranging from about 15° or less to about 45°.

I. An Apparatus for Vapor Deposition of Thin Coatings

Figure 1:
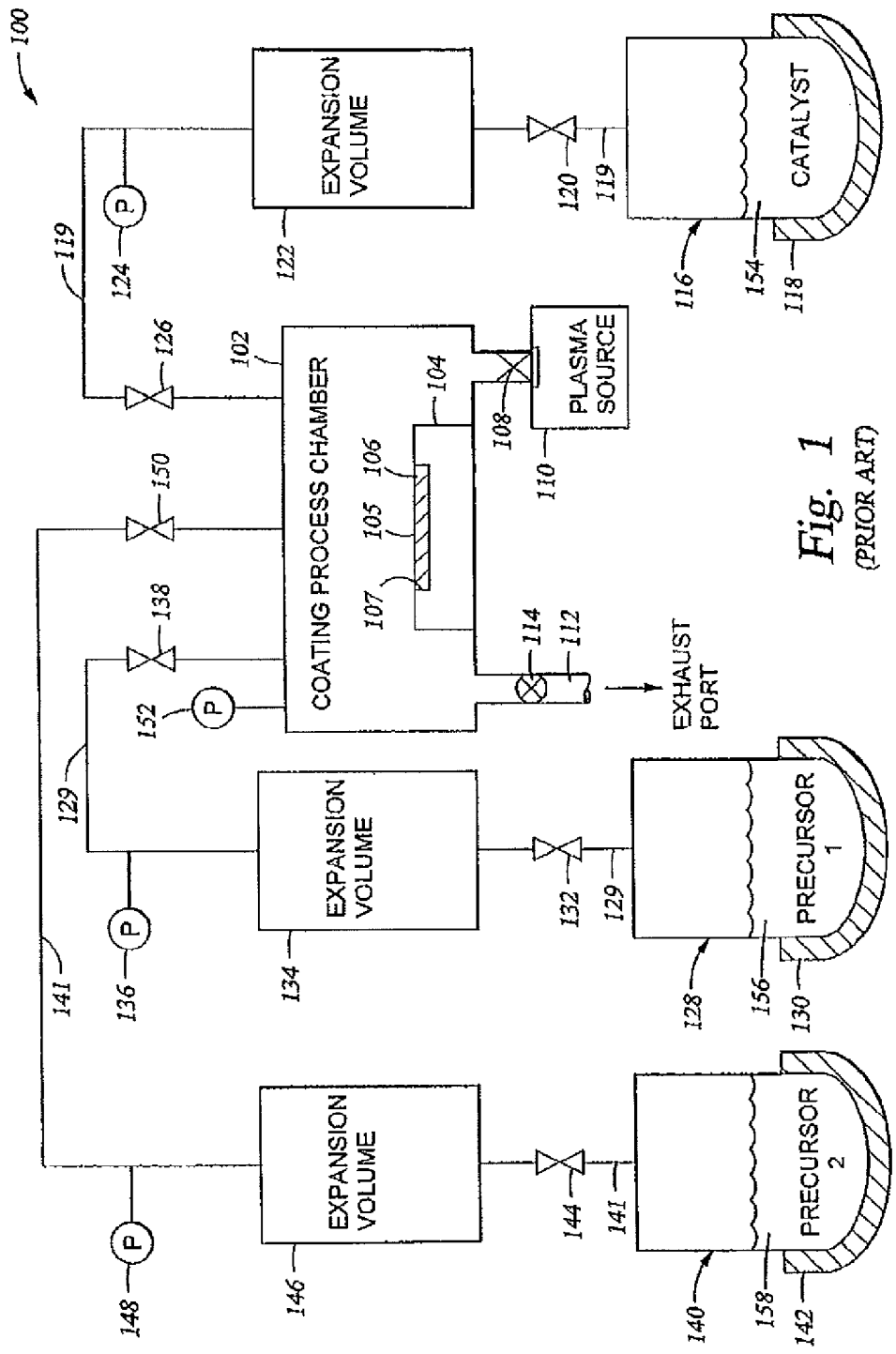
FIG. 1 shows a cross-sectional schematic of one embodiment of the kind of an apparatus which can be used to carry out a vapor deposition of a coating in accordance with the method of the present invention.

FIG. 1 shows a cross-sectional schematic of an apparatus 100 for vapor deposition of thin coatings. The apparatus 100 includes a process chamber 102 in which thin (typically 20 Å (2 nm) to 200 Å (20 nm) coatings, or thicker coatings in the range of about 200 Å (20 nm) to about 1 micron thick (1,000 nm) may be vapor deposited. A substrate 106 to be coated rests upon a temperature controlled substrate holder 104, typically within a recess 107 in the substrate holder 104.

Depending on the chamber design, the substrate 106 may rest on the chamber bottom (not shown in this position in FIG. 1). Attached to process chamber 102 is a remote plasma source 110, connected via a valve 108. Remote plasma source 110 may be used to provide a plasma which is used to clean and/or convert a substrate surface to a particular chemical state prior to application of a coating (which enables reaction of coating species and/or catalyst with the surface, thus improving adhesion and/or formation of the coating); or may be used to provide species helpful during formation of the coating (not shown) or modifications of the coating after deposition. The plasma may be generated using a microwave, DC, or inductive RF power source, or combinations thereof. The process chamber 102 makes use of an exhaust port 112 for the removal of reaction byproducts and is opened for pumping/purging the chamber 102. A shut-off valve or a control valve 114 is used to isolate the chamber or to control the amount of vacuum applied to the exhaust port. The vacuum source is not shown in FIG. 1.

The apparatus 100 shown in FIG. 1 is illustrative of a vapor deposited coating which employs two precursor materials and a catalyst. One skilled in the art will understand that one or more precursors and from zero to multiple catalysts may be used during vapor deposition of a coating. A catalyst storage container 116 contains catalyst 154, which may be heated using heater 118 to provide a vapor, as necessary. It is understood that precursor and catalyst storage container walls, and transfer lines into process chamber 102 will be heated as necessary to maintain a precursor or catalyst in a vaporous state, minimizing or avoiding condensation. The same is true with respect to heating of the interior surfaces of process chamber 102 and the surface of substrate 106 to which the coating (not shown) is applied. A control valve 120 is present on transfer line 119 between catalyst storage container 116 and catalyst vapor reservoir 122, where the catalyst vapor is permitted to accumulate until a nominal, specified pressure is measured at pressure indicator 124. Control valve 120 is in a normally-closed position and returns to that position once the specified pressure is reached in catalyst vapor reservoir 122. At the time the catalyst vapor in vapor reservoir 122 is to be released, valve 126 on transfer line 119 is opened to permit entrance of the catalyst present in vapor reservoir 122 into process chamber 102 which is at a lower pressure. Control valves 120 and 126 are controlled by a programmable process control system of the kind known in the art (which is not shown in FIG. 1).

A Precursor 1 storage container 128 contains coating reactant Precursor 1, which may be heated using heater 130 to provide a vapor, as necessary. As previously mentioned, Precursor 1 transfer line 129 and vapor reservoir 134 internal surfaces are heated as necessary to maintain a Precursor 1 in a vaporous state, minimizing and preferably avoiding condensation. A control valve 132 is present on transfer line 129 between Precursor 1 storage container 128 and Precursor 1 vapor reservoir 134, where the Precursor 1 vapor is permitted to accumulate until a nominal, specified pressure is measured at pressure indicator 136. Control valve 132 is in a normally closed position and returns to that position once the specified pressure is reached in Precursor 1 vapor reservoir 134. At the time the Precursor 1 vapor in vapor reservoir 134 is to be released, valve 138 on transfer line 129 is opened to permit entrance of the Precursor 1 vapor present in vapor reservoir 134 into process chamber 102, which is at a lower pressure. Control valves 132 and 138 are controlled by a programmable process control system of the kind known in the art (which is not shown in FIG. 1).

A Precursor 2 storage container 140 contains coating reactant Precursor 2, which may be heated using heater 142 to provide a vapor, as necessary. As previously mentioned, Precursor 2 transfer line 141 and vapor reservoir 146 internal surfaces are heated as necessary to maintain Precursor 2 in a vaporous state, minimizing, and preferably avoiding condensation. A control valve 144 is present on transfer line 141 between Precursor 2 storage container 146 and Precursor 2 vapor reservoir 146, where the Precursor 2 vapor is permitted to accumulate until a nominal, specified pressure is measured at pressure indicator 148. Control valve 141 is in a normally-closed position and returns to that position once the specified pressure is reached in Precursor 2 vapor reservoir 146. At the time the Precursor 2 vapor in vapor reservoir 146 is to be released, valve 150 on transfer line 141 is opened to permit entrance of the Precursor 2 vapor present in vapor reservoir 146 into process chamber 102, which is at a lower pressure. Control valves 144 and 150 are controlled by a programmable process control system of the kind known in the art (which is not shown in FIG. 1).

During formation of a coating (not shown) on a surface 105 of substrate 106, at least one incremental addition of vapor equal to the vapor reservoir 122 of the catalyst 154, and the vapor reservoir 134 of the Precursor 1, or the vapor reservoir 146 of Precursor 2 may be added to process chamber 102. The total amount of vapor added is controlled by both the adjustable volume size of each of the expansion chambers (typically 50 cc up to 1,000 cc) and the number of vapor injections (doses) into the reaction chamber. Further, the set pressure 124 for catalyst vapor reservoir 122, or the set pressure 136 for Precursor 1 vapor reservoir 134, or the set pressure 148 for Precursor 2 vapor reservoir 146, may be adjusted to control the amount (partial vapor pressure) of the catalyst or reactant added to any particular step during the coating formation process. This ability to control precise amounts of catalyst and vaporous precursors to be dosed (charged) to the process chamber 102 at a specified time provides not only accurate dosing of reactants and catalysts, but repeatability in the vapor charging sequence.

This apparatus provides a relatively inexpensive, yet accurate method of adding vapor phase precursor reactants and catalyst to the coating formation process, despite the fact that many of the precursors and catalysts are typically relatively non-volatile materials. In the past, flow controllers were used to control the addition of various reactants; however, these flow controllers may not be able to handle some of the precursors used for vapor deposition of coatings, due to the low vapor pressure and chemical nature of the precursor materials. The rate at which vapor is generated from some of the precursors is generally too slow to function with a flow controller in a manner which provides availability of material in a timely manner for the vapor deposition process.

The apparatus discussed above allows for accumulation of the specific quantity of vapor in the vapor reservoir which can be charged (dosed) to the reaction. In the event it is desired to make several doses during the coating process, the apparatus can be programmed to do so, as described above. Additionally, adding of the reactant vapors into the reaction chamber in controlled aliquots (as opposed to continuous flow) greatly reduces the amount of the reactants used and the cost of the coating.

One skilled in the art of chemical processing of a number of substrates simultaneously will recognize that a processing system which permits heat and mass transfer uniformly over a number of substrate surfaces simultaneously may be used to carry out the present invention.

II. Exemplary Embodiments of the Method of the Invention

A method of the invention provides for vapor-phase deposition of coatings, where at least one processing chamber (including an expansion volume and auxiliary valving and other apparatus) of the kind described above, or similar to the processing chamber described above is employed. Use of a processing chamber of the kind described in detail herein permits precise charging of vaporous reactive species which react with a substrate surface under stagnated conditions. The kind of processing chamber which provides for stagnated reaction may be used in combination with other kinds of process chambers which permit a continuous flow of reactant components across a substrate surface during coating deposition (not shown in drawings herein). This latter kind of processing chamber is commonly used in the art for chemical vapor deposition (CVD) of thin films, for example. A multi-chambered coating deposition system which employs a combination of the stagnation reaction processing chamber of the present invention with processing chambers of the kind used in the art for CVD, where substrates are moved between various processing chambers while the substrates are under a controlled environment, is contemplated.

Use of the stagnated reaction condition processing chamber of the kind described in detail herein permits precise charging of vaporous reactive species which react with a substrate surface under the stagnated conditions. This reaction under stagnated reaction conditions is employed during at least one individual deposition step to produce a given deposited layer, or is employed during deposition of at least one layer of a multilayered coating. Each coating precursor is transferred in vaporous form to a precursor vapor reservoir in which the precursor vapor accumulates. In the instance of simple, single-layer coatings, the vapor reservoir may be the processing chamber in which the coating is applied. A nominal amount of the precursor vapor, which is the amount required for a coating layer deposition is accumulated in the precursor vapor reservoir. The at least one coating precursor is charged from the precursor vapor reservoir into the processing chamber in which a substrate to be coated resides. In some instances at least one catalyst vapor is added to the process chamber in addition to the at least one precursor vapor, where the relative quantities of catalyst and precursor vapors are based on the physical characteristics to be exhibited by the coating. In some instances a diluent gas is added to the process chamber in addition to the at least one precursor vapor (and optional catalyst vapor). The diluent gas is chemically inert and is used to increase a total desired processing pressure, while the partial pressure amounts of coating precursors and optionally catalyst components are varied.

The example embodiments described below are with reference to formation of oxide coatings which exhibit a controlled degree of hydrophilicity; or, are with reference to use of a bonding oxide layer with an overlying silane-based polymeric layer or a bonding oxide with an overlying PEG polymeric layer to provide a hydrophobic surface on a substrate. However, it is readily apparent to one of skill in the art that the concepts involved can be applied to additional coating compositions and combinations which have different functionalities.

Due to the need to control the degree and scale of functionality of the coating at dimensions as small as Angstroms or nanometers, the surface preparation of the substrate prior to application of the coating is very important. One method of preparing the substrate surface is to expose the surface to a uniform, non-physically-bombarding plasma which is typically created from a plasma source gas containing oxygen. The plasma may be a remotely generated plasma which is fed into a processing chamber in which a substrate to be coated resides. Depending on the coating to be applied directly over the substrate, the plasma treatment of the substrate surface may be carried out in the chamber in which the coating is to be applied. This has the advantage that the substrate is easily maintained in a controlled environment between the time that the surface is treated and the time at which the coating is applied. Alternatively, it is possible to use a large system which includes several processing chambers and a centralized transfer chamber which allows substrate transfer from one chamber to another via a robot handling device, where the centralized handling chambers, as well as the individual processing chambers are each under a controlled environment.

To obtain the planned reaction on the initial, uncoated substrate surface, the initial substrate surface has to be prepared so that the reactivity of the surface itself with the vaporous components present in the process chamber will be as expected. The treatment may be a wet chemical clean, but is preferably a plasma treatment. Typically treatment with an oxygen plasma removes common surface contaminants. In some instances, it is necessary not only to remove contaminants from the substrate surface, but also to generate —OH functional groups on the substrate surface (in instances where such —OH functional groups are not already present).

When a silicon oxide layer is applied to the substrate surface to provide a substrate surface having a controlled hydrophobicity (a controlled availability of reactive hydroxylated sites) or hydrophilicity, the oxide layer may be created using the well-known catalytic hydrolysis of a chlorosilane, such as a tetrachlorosilane, in the manner previously described. A subsequent attachment of an organo-chlorosilane, which may or may not include a functional moiety, may be made to impart a particular function to the finished coating. By way of example and not by way of limitation, the hydrophobicity or hydrophilicity of the coating surface may be altered by the functional moiety present on a surface of an organo-chlorosilane which becomes the exterior surface of the coating.

The oxide layer, which may be silicon oxide or another oxide, may be formed using the method of the present invention by vapor phase hydrolysis of the chlorosilane, with subsequent attachment of the hydrolyzed silane to the substrate surface. Alternatively, the hydrolysis reaction may take place directly on the surface of the substrate, where moisture has been made available on the substrate surface to allow simultaneous hydrolyzation and attachment of the chlorosilane to the substrate surface.

By controlling the process parameters, both density of film coverage over the substrate surface and structural composition over the substrate surface are more accurately controlled, enabling the formation of very smooth films, which typically range from about 0.1 nm to less than about 15 nm, and even more typically from about 1 nm to about 5 nm in surface RMS roughness. For oxide films used to provide a hydrophilic surface, the thickness of the oxide film typically ranges from about 10 Å (1 nm) to about 200 Å (20 nm). When the oxide film is used as a structural (mechanically structural) and/or a bonding layer, the thickness of the layer may be greater, typically up to about 1,000 nm (1.0μ), and more typically up to about 500 nm (0.5μ). These films can be tailored in thickness, roughness, hydrophobicity/hydrophilicity, and density, which makes them particularly well suited for applications in the field of biotechnology and electronics. In addition, the structure of the films can be tailored to provide various functional coatings in general, particular where mechanical performance properties of the coating structure are important.

As previously discussed, oxide films deposited according to the present method can be used as bonding layers for subsequently deposited biocompatible coating materials, such as (for example and not by way of limitation) polyethylene glycol (PEG). The molecular weight of the polyethylene glycol will determine its physical characteristics (e.g., as the molecular weight increases, viscosity and freezing point increase). Polyethylene glycol is also available with varying numbers of functional (i.e., binding) groups, such as monofunctional (one binding group), difunctional (two binding groups), and multi-functional (more than two binding groups). The molecular weight and functionality of the polyethylene glycol will in combination determine the particular applications in which it is most useful. Polyethylene glycols which are useful in the present method typically range from about 400 to about 1000 in molecular weight.

Polyethylene glycol (with a structural formula: —($CH_2$—$CH_2$—O)—) is a well-known, non-toxic class of polymers useful in biotechnological and biomedical applications. For example, PEG is widely used as a drug coating, and as a component of many medications (e.g. laxatives, ophthalmic solutions and others). It has been studied in blood and issue engineering, as a material retarding bacterial growth and is widely used as a coating in analytical tools and in medical devices such as, for example, catheters or capillaries. PEG is known to be hydrophilic and to reduce adsorption of protein and lipid cells due to its highly hydrated surface. In the present instance, PEG is applied for surface treatment of substrates and devices which require hydrophilic, bio-compatible interfaces with body tissue and fluids or with biological reagents.

Example One

The vapor deposition techniques described previously herein were used to coat devices such as implantable (intraocular) lenses with a hydrophilic oxide/polyethylene glycol coating. Prior to deposition of the coating, the device surface was pre-treated by exposure to an oxygen plasma (150-200 sccm $O_2$ at an RF power of about 200 W and a process chamber pressure of 0.3 Torr in an Applied Micro-Structures' MVD™ process chamber) for 5 minutes in order to clean the surface and create hydroxyl availability on a substrate surface (by way of example and not by way of limitation).

Following oxygen plasma treatment of the lens, $SiCl_4$ was charged to the process chamber from a $SiCl_4$ vapor reservoir, where the $SiCl_4$ vapor pressure in the vapor reservoir was 18 Torr, creating a partial pressure of 2.3 Torr in the coating process chamber. Within 5 seconds, a first volume of $H_2O$ vapor was charged to the process chamber from a $H_2O$ vapor reservoir, where the $H_2O$ vapor pressure in the vapor reservoir was 18 Torr. A total of five reservoir volumes of $H_2O$ were charged, creating a partial pressure of 5.0 Torr in the coating process chamber. The total pressure in the coating process chamber was 7.3 Torr. The substrate temperature and the temperature of the process chamber walls was about 35° C. The substrate was exposed for a time period of about 10 minutes after the final $H_2O$ addition. The silicon oxide coating thickness obtained was about 100 Å.

To apply the PEG coating, methoxy(polyethyleneoxy)propyltrimethoxysilane (Gelest PIN SIM6492.7) (MW=450-600), was charged to the process chamber from a PEG vapor reservoir, where the PEG vapor pressure in the vapor reservoir was about 500 mTorr. Four reservoir volumes of PEG were charged, creating a partial pressure of 250 mTorr in the coating process chamber. After charging of the reservoir volumes, the substrate was exposed to the PEG precursor vapor for a time period of 15 minutes. No charging of water vapor from a reservoir to the process chamber is necessary with this PEG precursor. An alternative precursor which may be used to form a PEG coating is methoxy(polyethyleneoxy)propyltrichlorosilane (Gelest P/N SIM6492.66). However, use of this PEG precursor requires the addition of water vapor. The temperature of the process chamber walls was within the range of about 25° C. to about 60° C., and was most typically about 35° C. The PEG precursor source vessel and delivery line temperature was within the range of about 70° C. to about 110° C., and was most typically about 100° C. The PEG coating thickness obtained was about 20 Å (2 nm).

It is contemplated that any ethyleneoxy(ethylene glycol) terminated silylated precursor (silane) with the functional group R=HO($CH_2CH_2O)_nCH_2$— could be used with the present vapor deposition techniques, including, without limitation:

a chlorosilane or methoxysilane functionalized PEG-forming organosilicon derivative functionalized on either one or both PEG chain ends;

a poly(ethylene glycol) silane and bis-silane precursors; and an alkyltrichlorosilane ($RSiCl_3$) or alkyltrimethoxysilane ($RSi(OCH_3)_3$) precursor, where R contains ethylene glycol (oxide) groups.

Application of the PEG by a molecular vapor deposition process is performed in a vacuum. The application method steps include:

a) subjecting a surface which is planar or a surface having any one of a variety of three-dimensional shapes to an oxygen-comprising plasma in a processing chamber which is at a subatmospheric pressure ranging from about 0.1 Torr to about 1.0 Torr;

b) subsequently, without prior exposure of the oxygen-plasma-treated surface to ambient conditions which contaminate or react with the plasma-treated surface, exposing the surface to a silicon tetrachloride vapor in the presence of moisture, to form a thin (2 nm to 20 nm thick), hydrophilic silicon oxide (siloxane) layer on the surface;

c) subsequently, without prior exposure of the hydrophilic silicon oxide layer to ambient conditions which contaminate or react with the hydrophilic silicon oxide layer, exposing the oxide layer to a functionalized silane precursor vapor containing PEO/PEG groups, to react these groups with the hydrophilic silicon oxide layer, to form a layer selected from the group consisting of a monolayer, a self-aligned monolayer, and a polymerized cross-linked layer.

Optionally, repetition of one or more of the above-recited steps may be used, where an additional step is carried out:

d) repeating steps a) through c); or b) through c); or just c) a nominal number of times without exposing the substrate to ambient contaminants.

Typical process conditions for steps a) through c) in a process chamber of the kind previously described (having a volume of about 1.5 to about 2.0 liters) used in combination with a reservoir having a volume of about 300 cc are as follows. It is understood that one skilled in the art could adjust (scale) the process conditions provided below to accommodate a larger or smaller process chamber or a larger or smaller reservoir. For manufacturing operations, the process chamber (and coordinated reservoirs) would typically be considerably larger.

Step a): Plasma treatment of the substrate surface is carried out with an oxygen gas flow rate in the process chamber ranging from about 50 sccm to about 400 sccm when the process chamber volume is in the range of about 1.5-2.0 liters), with a process chamber pressure ranging from about 0.2 Torr to about 2.0 Torr. RF power to the plasma generation source is in the range of about 100 W to about 300 W, and the treatment time is about 1 minute to about 10 minutes, typically about 5 minutes.

Step b): $SiCl_4$ vapor is injected from a vapor reservoir of approximately 300 cc using an injection at a $SiCl_4$ vapor pressure of about 18 Torr. Subsequently, 5 injections of water vapor at 18 Torr from a vapor reservoir are added to the process chamber. In the alternative, a single injection of water vapor at 90 Torr may be used. The $SiCl_4$/water vapor combination is permitted to react with the surface for a time period ranging from about 1 minute to about 30 minutes, typically about 10 minutes. The film thickness may be adjusted by adjusting the amount of time the reaction is permitted to proceed.

Step c): PEG-comprising precursor deposition is carried out at a process chamber temperature ranging from about 25° C. to about 40° C., preferably at about 35° C. The PEG source and delivery line temperature typically ranges from about 70° C. to about 110° C., preferably the temperature is about 100° C. PEG-comprising precursor and other reactant vapors are injected from a vapor reservoir of approximately 300 cc.

Typically about 4 injections of PEG-comprising precursor at 500 mTorr reservoir pressure are made. When water vapor is used, water vapor is typically injected at this time, by way of example and not by way of limitation. The reaction time period for the PEG-comprising precursor or the combination of reactants is in the range of about 5 minutes to 30 minutes, typically about 15 minutes.

Two PEG-comprising precursors were evaluated, 2-[methoxy(polyethyleneoxy)propyl]heptamethyltrisiloxane $(C_{11}H_{30}O_3Si_3(C_2H_4O)_{6-9}CH_3$; and 2-[methoxy(polyethyleneoxy)propyl]trimethoxysilane $(CH_3(OC_2H_4)_{6-9}(CH_2)_3OSi(OCH_3)_3$. The resulting DI water contact angle on a substrate prepared in the manner described above, with respect to each precursor, was about 32 degrees on a silicon substrate and 22 degrees on an acrylic substrate.

Table 1 below provides test data for the silicon substrate and acrylic substrates in the form of lenses, with oxide and PEG-comprising coating layers applied in the manner described above.

TABLE 1

| Run Order | $SiO_2$ (Å) | PEG coating cycles | Si Subst flat Contact Angle (°) | Acr Subst flat Contact Angle (°) | Appearance of five coated lenses (transmission) |
|---|---|---|---|---|---|
| 1 | none | 8 | 27 | 38 | acceptable |
| 2 | 20 | 4 | 8 | 26 | acceptable |
| 3 | 20 | 8 | 21 | 31 | acceptable |
| 4 | 60 | 4 | 26 | 23 | acceptable |
| 5 | 400 | none | <5 | <5 | not acceptable |
| 6 | none | 4 | 10 | 29 | acceptable |
| 7 | none | 2 | 7 | 32 | acceptable |
| 8 | 20 | none | <5 | 31 | acceptable |
| 9 | 20 | 2 | 8 | 29 | acceptable |
| 10 | 150 | none | <5 | <5 | not acceptable |
| 11 | 60 | 2 | 20 | 20 | acceptable |
| 12 | 60 | 8 | 28 | 28 | not tested |
| 13 | none | none | <5 | 33 | — |
| 14 | 150 | 4 | 26 | 19 | acceptable |
| 15 | 60 | none | <5 | 17 | not tested |
| 16 | 150 | 4 | 26 | 16 | not tested |

Oxide/polyethylene glycol coatings providing hydrophilicity can also be deposited, using the present method, over the surfaces of other medical devices and implants, including those which are intended for temporary use (such as contact lenses and catheters, for example and without limitation) and those which are intended for "permanent" (i.e., at least 5 to 10 years) implantation (such as intra-ocular lenses, synthetic blood vessels and heart valves, stents, joint (such as a hip or knee) or hard tissue (i.e., bone or cartilage) replacements, and breast implants, for example and without limitation) within the body. The application of a hydrophilic oxide/PEG coating over surfaces of the medical device or implant improves both the hydrophilicity and biocompatibility of the device/implant.

In instances where it is desired to create multilayered coatings, for example and not by way of limitation, it is advisable to use oxygen plasma treatment prior to and between PEO/PEG coating deposition steps. This oxygen plasma treatment activates dangling bonds on the substrate surface, which dangling bonds may be exposed to a controlled partial pressure of water vapor to create a new concentration of OH reactive sites on the substrate surface. The PEO/PEG coating deposition process may then be repeated, increasing the coating thickness.

A computer-driven process control system may be used to provide for a series of additions of reactants to the process chamber in which the layer or coating is being formed. This process control system typically also controls other process variables, such as (for example and not by way of limitation), total process chamber pressure (typically less than atmospheric pressure), substrate temperature, temperature of process chamber walls, temperature of the vapor delivery manifolds, processing time for given process steps, and other process parameters if needed.

The hydrolysis in the vapor phase using relatively wide range of partial pressure of the silicon tetrachloride precursor in combination with a partial pressure in the range of 10 Torr or greater of water vapor will generally result in rougher surfaces on the order of 5 nm RMS or greater, where the thickness of the film formed will typically be in the range of about 20 nm or greater. Thinner films of the kind enabled by one of the embodiments of applicants' invention typically exhibit a 1-5 nm RMS finish and are grown by carefully balancing the vapor and surface hydrolysis reaction components. For example, and not by way of limitation, for a thin film of an oxide-based layer, prepared on a silicon substrate, where the oxide-based layer exhibits a thickness ranging from about 2 nut to about 15 nm, typically the oxide-based layer exhibits a 1-5 nm RMS finish.

We have obtained such films in an apparatus of the kind previously described, where the partial pressure of the silicon tetrachloride is in the range of about 0.5 to 4.0 Torr, the partial pressure of the water vapor is in the range of about 2 to about 8 Torr, where the total process chamber pressure ranges from about 3 Torr to about 10 Torr, where the substrate temperature ranges from about 20° C. to about 60° C., where the process chamber walls are at a temperature ranging from about 30° C. to about 60° C., and where the time period over which the substrate is exposed to the combination of silicon tetrachloride and water vapor ranges from about 2 minutes to about 12 minutes. This deposition process will be described in more detail subsequently herein, with reference to FIGS. 6A through 6C.

A multilayered coating process may include plasma treatment of the surface of one deposited layer prior to application of an overlying layer. Typically, the plasma used for such treatment is a low density plasma. This plasma may be a remotely generated plasma. The most important feature of the treatment plasma is that it is a "soft" plasma which affects the exposed surface enough to activate the surface of the layer being treated, but not enough to etch through the layer. The apparatus used to carry out the method provides for the addition of a precise amount of each of the reactants to be consumed in a single reaction step of the coating formation process. The apparatus may provide for precise addition of different combinations of reactants during each individual step when there are a series of different individual steps in the coating formation process. Some of the individual steps may be repetitive.

One example of the application of the method described here is deposition of a multilayered coating including at least one oxide-based layer. The thickness of the oxide-based layer depends on the end-use application for the multilayered coating. The oxide-based layer (or a series of oxide-based layers alternated with organic-based layers) may be used to increase the overall thickness of the multilayered coating (which typically derives the majority of its thickness from the oxide-based layer), and depending on the mechanical properties to be obtained, the oxide-based layer content of the multilayered coating may be increased when more coating rigidity and abrasion resistance is required.

The oxide-based layer is frequently used to provide a bonding surface for subsequently deposited various molecular organic-based coating layers. When the surface of the oxide-based layer is one containing —OH functional groups, the organic-based coating layer typically includes, for example and not by way of limitation, a silane-based functionality which permits covalent bonding of the organic-based coating layer to —OH functional groups present on the surface of the oxide-based layer. When the surface of the oxide-based layer is one capped with halogen functional groups, such as chlorine, by way of example and not by way of limitation, the organic-based coating layer includes, for example, an —OH functional group, which permits covalent bonding of the organic-based coating layer to the oxide-based layer functional halogen group.

By controlling the precise thickness, chemical, and structural composition of an oxide-based layer on a substrate, for example, we are able to direct the coverage and the functionality of a coating applied over the bonding oxide layer. The coverage and functionality of the coating can be controlled over the entire substrate surface on a nm scale. Specific, different thicknesses of an oxide-based substrate bonding layer are required on different substrates. Some substrates require an alternating series of oxide-based/organic-based layers to provide surface stability for a coating structure.

With respect to substrate surface properties, such as hydrophobicity or hydrophilicity, for example, a silicon wafer surface becomes hydrophilic, to provide a less than 5 degree water contact angle, after plasma treatment when there is some moisture present. Not much moisture is required, for example, typically the amount of moisture present after pumping a chamber from ambient air down to about 15 mTorr to 20 mTorr is sufficient moisture. A stainless steel surface requires formation of an overlying oxide-based layer having a thickness of about 30 Å or more to obtain the same degree of hydrophilicity as that obtained by plasma treatment of a silicon surface. Glass and polystyrene materials become hydrophilic, to a 5 degree water contact angle, after the application of about 80 Å or more of an oxide-based layer. An acrylic surface requires about 150 Å or more of an oxide-based layer to provide a 5 degree water contact angle.

There is also a required thickness of oxide-based layer to provide a good bonding surface for reaction with a subsequently applied organic-based layer. By a good bonding surface, it is meant a surface which provides full, uniform surface coverage of the organic-based layer. By way of example, about 80 Å or more of a oxide-based substrate bonding layer over a silicon wafer substrate provides a uniform hydrophobic contact angle, about 112 degrees, upon application of a SAM organic-based layer deposited from an FDTS (perfluorodecyltrichlorosilanes) precursor. About 150 Å or more of oxide-based substrate bonding layer is required over a glass substrate or a polystyrene substrate to obtain a uniform coating having a similar contact angle. About 400 Å or more of oxide-based substrate bonding layer is required over an acrylic substrate to obtain a uniform coating having a similar contact angle.

The organic-based layer precursor, in addition to containing a functional group capable of reacting with the oxide-based layer to provide a covalent bond, may also contain a functional group at a location which will form the exterior surface of the attached organic-based layer. This functional group may subsequently be reacted with other organic-based precursors, or may be the final layer of the coating and be used to provide surface properties of the coating, such as to render the surface hydrophobic or hydrophilic, by way of example and not by way of limitation. The functionality of an attached organic-based layer may be affected by the chemical composition of the previous organic-based layer (or the chemical composition of the initial substrate) if the thickness of the oxide layer separating the attached organic-based layer from the previous organic-based layer (or other substrate) is inadequate. The required oxide-based layer thickness is a function of the chemical composition of the substrate surface underlying the oxide-based layer, as illustrated above. In some instances, to provide structural stability for the surface layer of the coating, it is necessary to apply several alternating layers of an oxide-based layer and an organic-based layer.

With reference to chlorosilane-based coating systems of the kind described in the Background Art section of this application, where one end of the organic molecule presents chlorosilane, and the other end of the organic molecule presents a fluorine moiety, after attachment of the chlorosilane end of the organic molecule to the substrate, the fluorine moiety at the other end of the organic molecule provides a hydrophobic coating surface. Further, the degree of hydrophobicity and the uniformity of the hydrophobic surface at a given location across the coated surface may be controlled using the oxide-based layer which is applied over the substrate surface prior to application of the chlorosilane-comprising organic molecule. By controlling the oxide-based layer application, the organic-based layer is controlled indirectly. For example, using the process variables previously described, we are able to control the concentration of OH reactive species on the substrate surface. This, in turn, controls the density of reaction sites needed for subsequent deposition of a silane-based polymeric coating. Control of the substrate surface active site density enables uniform growth and application of high density self-aligned monolayer coatings (SAMS), for example.

We have discovered that it is possible to convert a hydrophilic-like substrate surface to a hydrophobic surface by application of an oxide-based layer of the minimal thickness described above with respect to a given substrate, followed by application of an organic-based layer over the oxide-based layer, where the organic-based layer provides hydrophobic surface functional groups on the end of the organic molecule which does not react with the oxide-based layer. However, when the initial substrate surface is a hydrophobic surface and it is desired to convert this surface to a hydrophilic surface, it is necessary to use a structure which comprises more than one oxide-based layer to obtain stability of the applied hydrophilic surface in water. It is not just the thickness of the oxide-based layer or the thickness of the organic-based layer which is controlling. The structural stability provided by a multilayered structure of repeated layers of oxide-based material interleaved with organic-based layers provides excellent results.

After deposition of a first organic-based layer, and prior to the deposition of a subsequent layer in a multilayered coating, it is advisable to use an in-situ oxygen plasma treatment. This treatment activates reaction sites of the first organic-based layer and may be used as part of a process for generating an oxide-based layer or simply to activate dangling bonds on the substrate surface. The activated dangling bonds may be exploited to provide reactive sites on the substrate surface. For example, an oxygen plasma treatment in combination with a controlled partial pressure of water vapor may be used to create a new concentration of OH reactive species on an exposed surface. The activated surface is then used to provide covalent bonding with the next layer of material applied. A deposition process may then be repeated, increasing the total coating thickness, and eventually providing a surface layer having the desired surface properties. In some instances, where the substrate surface includes metal atoms, treatment with the oxygen plasma and moisture provides a metal oxide-based layer containing —OH functional groups. This oxide-based layer is useful for increasing the overall thickness of the multilayered coating and for improving mechanical strength and rigidity of the multilayered coating.

Following the deposition of a multilayered coating as described above, a surface oxide layer can be used as a bonding layer for subsequent deposition of biocompatible coating materials, such as (for example and not by way of limitation) polyethylene glycol (PEG). Polyethylene glycol can be deposited using molecular vapor deposition (MVD™) to provide a surface layer over underling layers of other materials.

Example Two

Deposition of a Silicon Oxide Layer Having a Controlled Number of OH
Reactive Sites Available On the Oxide Layer Surface A technique for adjusting the hydrophobicity/hydrophilicity of a substrate surface (so that the surface is converted from hydrophobic to hydrophilic or so that a hydrophilic surface is made more hydrophilic, for example) may also be viewed as adjusting the number of OH reactive sites available on the surface of the substrate. One such technique is to apply an oxide coating over the substrate surface while providing the desired concentration of OH reactive sites available on the oxide surface. A schematic 200 of the mechanism of oxide formation in shown in FIG. 2. In particular, a substrate 202 has OH groups 204 present on the substrate surface 203. A chlorosilane 208, such as the tetrachlorosilane shown, and water 206 are reacted with the OH groups 204, either simultaneously or in sequence, to produce the oxide layer 205 shown on surface 203 of substrate 202 and byproduct HCl 210. In addition to chlorosilane precursors, chlorosiloxanes, fluorosilanes, and fluorosiloxanes may be used.

Subsequently, the surface of the oxide layer 205 can be further reacted with water 216 to replace Cl atoms on the upper surface of oxide layer 205 with OH groups 217, to produce the hydroxylated layer 215 shown on surface 203 of substrate 202 and byproduct HCl 220. By controlling the amount of water used in both reactions, the frequency of OH reactive sites available on the oxide surface is controlled.

Example Three

In the preferred embodiment discussed below, the silicon oxide coating was applied over a glass substrate. The glass substrate was treated with an oxygen plasma in the presence of residual moisture which was present in the process chamber (after pump down of the chamber to about 20 mTorr) to provide a clean surface (free from organic contaminants) and to provide the initial OH groups on the glass surface.

Various process conditions for the subsequent reaction of the OH groups on the glass surface with vaporous tetrachlorosilane and water are provided below in Table 2, along with data related to the thickness and roughness of the oxide coating obtained and the contact angle (indicating hydrophobicity/hydrophilicity) obtained under the respective process conditions. A lower contact angle indicates increased hydrophilicity and an increase in the number of available OH groups on the silicon oxide surface.

TABLE 2

Deposition of a Silicon Oxide Layer of Varying Hydrophilicity

| Run No. | Order of Dosing | Partial Pressure SiCl$_4$ Vapor (Torr) | Partial Pressure H$_2$O Vapor (Torr) | Reaction Time (min.) | Coating Thickness (nm) | Coating Roughness (RMS, nm)* | SiO$_2$ Contact Angle*** (°) |
|---|---|---|---|---|---|---|---|
| 1 | First[2] SiCl$_4$ | 0.8 | 4 | 10 | 3 | 1 | <5 |
| 2 | First[1] H$_2$O | 4 | 10 | 10 | 35 | 5 | <5 |
| 3 | First[2] SiCl$_4$ | 4 | 10 | 10 | 30 | 4 | <5 |
| 1 | First[3] FOTS | 0.2 | 0.8 | 15 | 4 | 1 | 108 |
| 2 | First[3] FOTS | 0.2 | 0.8 | 15 | 36 | 5 | 109 |

TABLE 2-continued

Deposition of a Silicon Oxide Layer of Varying Hydrophilicity

| Run No. | Order of Dosing | Partial Pressure SiCl$_4$ Vapor (Torr) | Partial Pressure H$_2$O Vapor (Torr) | Reaction Time (min.) | Coating Thickness (nm) | Coating Roughness (RMS, nm)* | SiO$_2$ Contact Angle*** (°) |
|---|---|---|---|---|---|---|---|
| 3 | First[3] FOTS | 0.2 | 0.8 | 15 | 31 | 4 | 109 |

*Coating roughness is the RMS roughness measured by AFM (atomic force microscopy).
**The FOTS coating layer was a monolayer which added ≈1 nm in thickness.
***Contact angles were measured with 18 MΩ D.I. water.
[1] The H$_2$O was added to the process chamber 10 seconds before the SiCl$_4$ was added to the process chamber.
[2] The SiCl$_4$ was added to the process chamber 10 seconds before the H$_2$O was added to the process chamber.
[3] The FOTS was added to the process chamber 5 seconds before the H$_2$O was added to the process chamber.
[4] The substrate temperature and the chamber wall temperature were each 35° C. for both application of the SiO$_2$ bonding/bonding layer and for application of the FOTS organo-silane over-lying monolayer (SAM) layer.

We have discovered that very different film thicknesses and film surface roughness characteristics can be obtained as a function of the partial pressures of the precursors, despite the maintenance of the same time period of exposure to the precursors. Table 3 below illustrates this unexpected result.

TABLE 3

Response Surface Design* Silicon Oxide Layer Deposition

| Run No. | Total Pressure (Torr) | Partial Pressure SiCl$_4$ Vapor (Torr) | Partial Pressure H$_2$O Vapor (Torr) | Substrate and Chamber Wall Temp. (° C.) | Reaction Time (min.) | Coating Thickness (nm) | Coating Surface Roughness RMS (nm) |
|---|---|---|---|---|---|---|---|
| 1 | 9.4 | 2.4 | 7 | 35 | 7 | 8.8 | NA |
| 2 | 4.8 | 0.8 | 4 | 35 | 7 | 2.4 | 1.29 |
| 3 | 6.4 | 2.4 | 4 | 35 | 4 | 3.8 | 1.39 |
| 4 | 14 | 4 | 10 | 35 | 7 | 21.9 | NA |
| 5 | 7.8 | 0.8 | 7 | 35 | 4 | 4 | 2.26 |
| 6 | 11 | 4 | 7 | 35 | 10 | 9.7 | NA |
| 7 | 11 | 4 | 7 | 35 | 4 | 10.5 | NA |
| 8 | 12.4 | 2.4 | 10 | 35 | 4 | 14 | NA |
| 9 | 6.4 | 2.4 | 4 | 35 | 10 | 4.4 | 1.39 |
| 10 | 9.4 | 2.4 | 7 | 35 | 7 | 8.7 | NA |
| 11 | 12.4 | 2.4 | 10 | 35 | 10 | 18.7 | NA |
| 12 | 9.4 | 2.4 | 7 | 35 | 7 | 9.5 | NA |
| 13 | 8 | 4.8 | 4 | 35 | 7 | 6.2 | 2.16 |
| 14 | 10.8 | 0.8 | 10 | 35 | 7 | 6.9 | NA |
| 15 | 7.8 | 0.8 | 7 | 35 | 10 | 4.4 | 2.24 |

*(Box-Behnken) 3 Factors, 3 Center Points
NA = Not Available, Not Measured

In addition to the tetrachlorosilane described above as a precursor for oxide formation, other chlorosilane precursors such a trichlorosilanes, dichlorosilanes work well as a precursor for oxide formation. Examples of specific advantageous precursors include hexachlorodisilane (Si$_2$Cl$_6$) and hexachlorodisiloxane (Si$_2$Cl$_6$O). As previously mentioned, in addition to chlorosilanes, chlorosiloxanes, fluorosilanes, and fluorosiloxanes may also be used as precursors.

Similarly, the vapor deposited silicon oxide coating from the SiCl$_4$ and H$_2$O precursors was applied over glass, polycarbonate, acrylic, polyethylene and other plastic materials using the same process conditions as those described above with reference to the silicon substrate. Prior to application of the silicon oxide coating, the surface to be coated was treated with an oxygen plasma.

Figure 2:
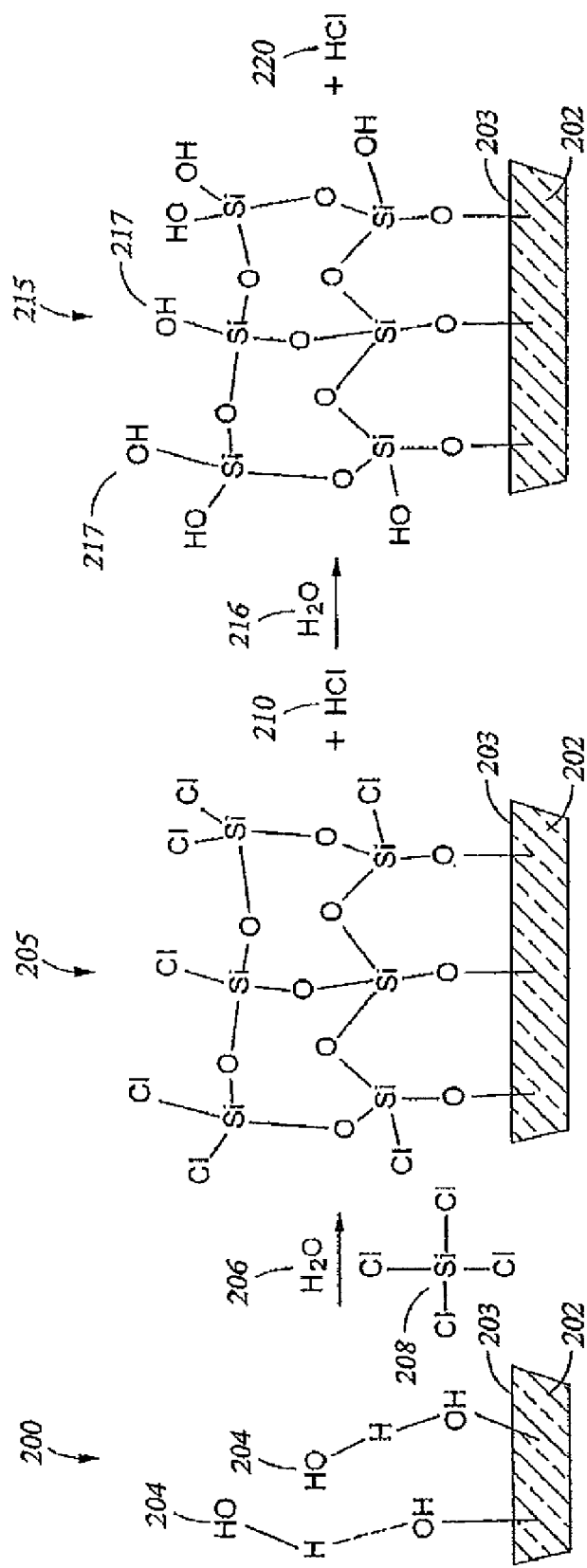
FIG. 2 is a schematic which shows the reaction mechanism where tetrachlorosilane and water are reacted with a substrate which exhibits active hydroxyl groups on the substrate surface, to form a silicon oxide layer on the surface of the substrate.

A silicon oxide coating of the kind described above can be applied over a self aligned monolayer (SAM) coating formed from an organic precursor, for example and not by way of limitation from fluoro-tetrahydrooctyldimethylchlorosilane (POTS). Prior to application of the silicon oxide coating, the surface of the SAM should be treated with an oxygen plasma. A FOTS coating surface requires a plasma treatment of about 10-30 seconds to enable adhesion of the silicon oxide coating. The plasma treatment creates reactive OH sites on the surface of the SAM layer, which sites can subsequently be reacted with SiCl$_4$ and water precursors, as illustrated in FIG. 2, to create a silicon oxide coating. This approach allows for deposition of multi-layered molecular coatings, where all of the layers may be the same, or some of the layers may be different, to provide particular performance capabilities for the multi-layered coating.

Functional properties designed to meet the end use application of the finalized product can be tailored by either sequentially adding an organo-silane precursor to the oxide coating precursors or by using an organo-silane precursor(s) for formation of the last, top layer coating. Organo-silane precursor materials may include functional groups such that the silane precursor includes an alkyl group, an alkoxyl group, an alkyl substituted group containing fluorine, an alkoxyl substituted group containing fluorine, a vinyl group, an ethynyl group, or a substituted group containing a silicon atom or an oxygen atom, by way of example and not by way of limitation. In particular, organic-containing precursor materials such as (and not by way of limitation) silanes, chlorosilanes, fluorosilanes, methoxy silanes, alkyl silanes, amino silanes, epoxy silanes, glycoxy silanes, and acrylosilanes are useful in general.

Some of the particular precursors used to produce coatings are, by way of example and not by way of limitation, perfluorodecyltrichlorosilanes (FDTS), undecenyltrichlorosilanes (UTS), vinyl-trichlorosilanes (VTS), decyltrichlorosilanes (DTS), octadecyltrichlorosilanes (OTS), ditnethyldichlorosilanes (DDMS), dodecenyltricholrosilanes (DDTS), fluorotetrahydrooctyldimethylchlorosilanes (POTS), perfluoroodyldimethylchlorosilanes, aminopropylmethoxysilanes (APTMS), fluoropropylmethyldiclorosilanes, and perfluorodecyldimethylchlorosilanes. The OTS, DTS, UTS, YTS, DDTS, FOTS, and FDTS are all trichlorosilane precursors. The other end of the precursor chain is a saturated hydrocarbon with respect to OTS, DTS, and UTS; contains a vinyl functional group, with respect to VTS and DDTS; and contains fluorine atoms with respect to FDTS (which also has fluorine atoms along the majority of the chain length). Other useful precursors include 3-aminopropyltrimethoxysilane (APTMS), which provides amino functionality, and 3-glycidoxypropyltrimethoxysilane (GPTMS). One skilled in the art of organic chemistry can see that the vapor deposited coatings from these precursors can be tailored to provide particular functional characteristics for a coated surface.

Most of the silane-based precursors, such as commonly used di- and tri-chlorosilanes, for example and not by way of limitation, tend to create agglomerates on the surface of the substrate during the coating formation. These agglomerates can cause structure malfunctioning or stiction. Such agglomerations are produced by partial hydrolysis and polycondensation of the polychlorosilanes. This agglomeration can be prevented by precise metering of moisture in the process ambient which is a source of the hydrolysis, and by carefully controlled metering of the availability of the chlorosilane precursors to the coating formation process. The carefully metered amounts of material and careful temperature control of the substrate and the process chamber walls can provide the partial vapor pressure and condensation surfaces necessary to control formation of the coating on the surface of the substrate rather than promoting undesired reactions in the vapor phase or on the process chamber walls.

Example Four

When the oxide-forming silane and the organo-silane which includes the functional moiety are deposited simultaneously (co-deposited), the reaction may be so rapid that the sequence of precursor addition to the process chamber becomes critical. For example, in a co-deposition process of $SiCl_4$/FOTS/$H_2O$, if the FOTS is introduced first, it deposits on the glass substrate surface very rapidly in the form of islands, preventing the deposition of a homogeneous composite film. Examples of this are provided in Table 4, below.

When the oxide-forming silane is applied to the substrate surface first, to form the oxide layer with a controlled density of potential OH reactive sites available on the surface, the subsequent reaction of the oxide surface with a FOTS precursor provides a uniform film without the presence of agglomerated islands of polymeric material, examples of this are provided in Table 4 below.

TABLE 4

Deposition of a Coating Upon a Silicon Substrate*
Using Silicon Tetrachloride and FOTS Precursors

| Run No. | Total Pressure (Torr) | Partial Pressure $SiCl_4$ Vapor (Torr) | Partial Pressure FOTS Vapor (Torr) | Partial Pressure $H_2O$ Vapor (Torr) | Substrate and Chamber Wall Temp. (° C.) |
|---|---|---|---|---|---|
| 1 FOTS + $H_2O$ | 1 | — | 0.2 | 0.8 | 35 |
| 2 $H_2O$ + $SiCl_4$ followed by FOTS + $H_2O$ | 141 | 4 | — 0.20 | 100.8 | 3535 |
| 3 FOTS + $SiCl_4$ + $H_2O$ | 14.2 | 4 | 0.2 | 10 | 35 |
| 4 $SiCl_4$ + $H_2O$ | 14 | 4 | — | 10 | 35 |
| 5 $SiCl_4$ + $H_2O$ | 5.8 | 0.8 | — | 5 | 35 |
| 6 $SiCl_4$ + $H_2O$ repeated twice | 14 | 4 | — | 10 | 35 |

An example process description for Run No. 2 was as follows.

Step 1. Pump down the reactor and purge out the residual air and moisture to a final baseline pressure of about 30 mTorr or less.

Step 2. Perform $O_2$, plasma clean of the substrate surface to eliminate residual surface contamination and to oxygenate/hydroxylate the substrate. The cleaning plasma is an oxygen-containing plasma. Typically the plasma source is a remote plasma source, which may employ an inductive power source. However, other plasma generation apparatus may be used. In any case, the plasma treatment of the substrate is typically carried out in the coating application process chamber. The plasma density/efficiency should be adequate to provide a substrate surface after plasma treatment which exhibits a contact angle of about 10° or less when measured with 18 MΩD.I. water. The coating chamber pressure during plasma treatment of the substrate surface in the coating chamber was 0.5 Torr, and the duration of substrate exposure to the plasma was 5 minutes.

Step 3. Inject $SiCl_4$ and within 10 seconds inject water vapor at a specific partial pressure ratio to the $SiCl_4$, to form a silicon oxide base layer on the substrate. For example, for the glass substrate discussed in Table III, 1 volume (300 cc at 100 Torr) of $SiCl_4$ to a partial pressure of 4 Torr was injected, then, within 10 seconds 10 volumes (300 cc at 17 Torr each) of water vapor were injected to produce a partial pressure of 10 Torr in the process chamber, so that the volumetric pressure ratio of water vapor to silicon tetrachloride is about 2.5. The substrate was exposed to this gas mixture for 1 min to 15 minutes, typically for about 10 minutes. The substrate temperature in the examples described above was in the range of about 35° C. Substrate temperature may be in the range from about 20° C. to about 80° C. The process chamber surfaces were also in the range of about 35° C.

Step 4. Evacuate the reactor to <30 mTorr to remove the reactants.

Step 5. Introduce the chlorosilane precursor and water vapor to form a hydrophobic coating. In the example in Table III, FOTS vapor was injected first to the charging reservoir, and then into the coating process chamber, to provide a FOTS partial pressure of 200 mTorr in the process chamber, then, within 10 seconds, $H_2O$ vapor (300 cc at 12 Torr) was injected to provide a partial pressure of about 800 mTorr, so that the total reaction pressure in the chamber was 1 Torr. The substrate was exposed to this mixture for 5 to 30 minutes, typically 15 minutes, where the substrate temperature was about 35° C. Again, the process chamber surface was also at about 35° C.

An example process description for Run No. 3 was as follows.

Step 1. Pump down the reactor and purge out the residual air and moisture to a final baseline pressure of about 30 mTorr or less.

Step 2. Perform remote $O_2$ plasma clean to eliminate residual surface contamination and to oxygenate/hydroxylate the glass substrate. Process conditions for the plasma treatment were the same as described above with reference to Run No. 2.

Step 3. Inject FOTS into the coating process chamber to produce a 200 mTorr partial pressure in the process chamber. Then, inject 1 volume (300 cc at 100 Torr) of $SiCl_4$ from a vapor reservoir into the coating process chamber, to a partial pressure of 4 Torr in the process chamber. Then, within 10 seconds, inject ten volumes (300 cc at 17 Torr each) of water vapor from a vapor reservoir into the coating process chamber, to a partial pressure of 10 Torr in the coating process chamber. Total pressure in the process chamber is then about 14 Torr. The substrate temperature was in the range of about 35° C. for the specific examples described, but could range from about 15° C. to about 80° C. The substrate was exposed to this three gas mixture for about 1-15 minutes, typically about 10 minutes.

Step 4. Evacuate the process chamber to a pressure of about 30 mTorr to remove excess reactants.

Example Five

Figure 3A:
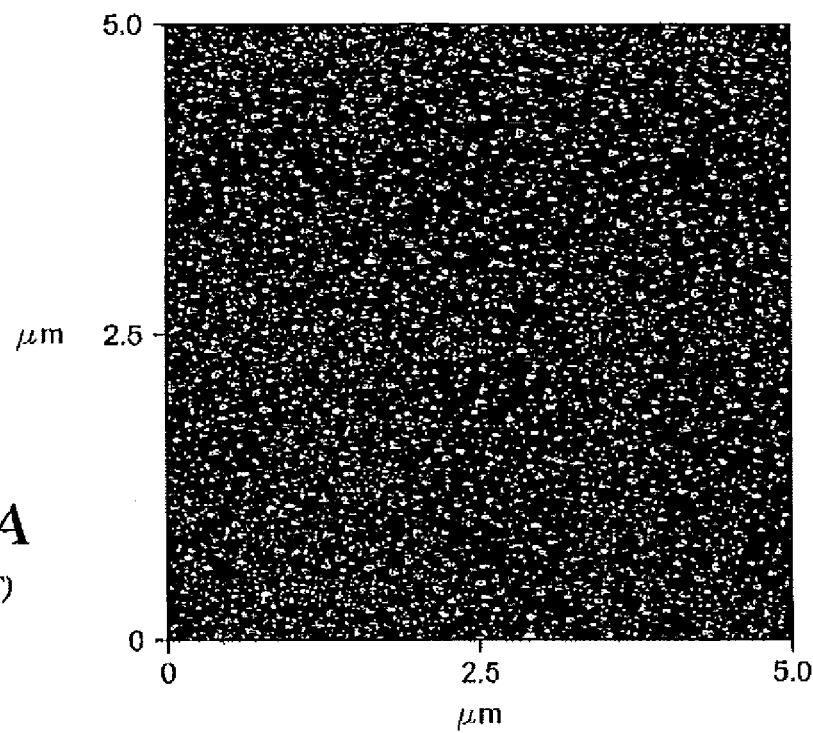
FIGS. 3A and 3B show schematics of atomic force microscope (AFM) images of silicon oxide bonding layers deposited on a silicon substrate. The initial silicon substrate surface RMS roughness measured less than about 0.1 nm.
Figure 3B:
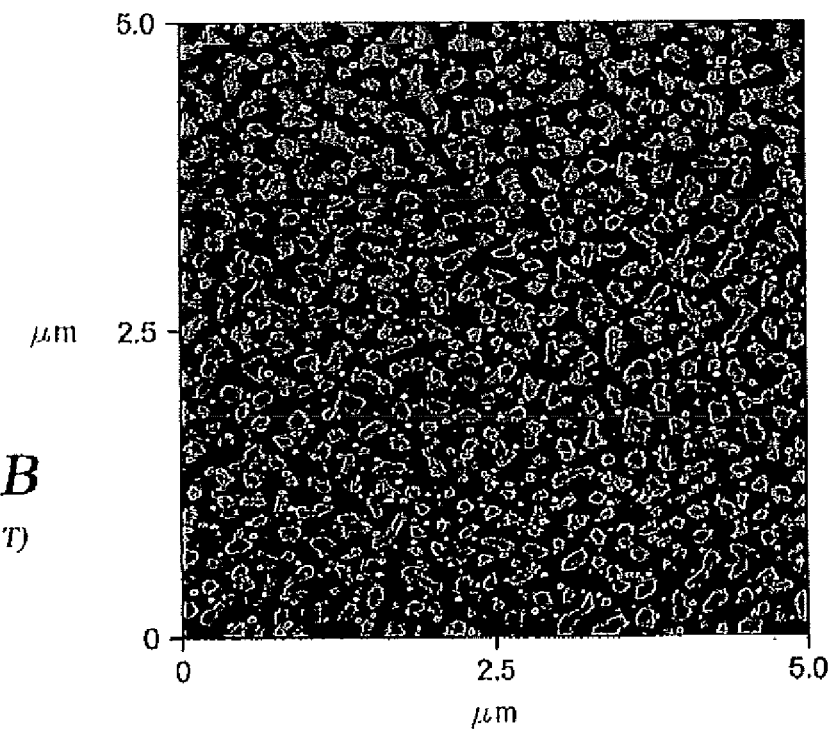

FIGS. 3A and 3B are schematics of AFM (atomic force microscope) images of surfaces of silicon oxide bonding coatings as applied over a silicon substrate. The initial silicon substrate surface RMS roughness was determined to be less than about 0.1 nm. FIG. 3A illustrates a deposition process in which the substrate was silicon. The surface of the silicon was exposed to an oxygen plasma in the manner previously described herein for purposes of cleaning the surface and creating hydroxyl availability on the silicon surface. $SiCl_4$ was charged to the process chamber from a $SiCl_4$ vapor reservoir, creating a partial pressure of 0.8 Torr in the coating process chamber. Within 10 seconds, $H_2O$ vapor was charged to the process chamber from a $H_2O$ vapor reservoir, creating a partial pressure of 4 Torr in the coating process chamber. The total pressure in the coating process chamber was 4.8 Torr. The substrate temperature and the temperature of the process chamber walls was about 35° C. The substrate was exposed to the mixture of $SiCl_4$ and $H_2O$ for a time period of 10 minutes. The silicon oxide coating thickness obtained was about 3 nm. The coating roughness in RMS was 1.4 nm and Ra was 0.94 nm.

FIG. 3B illustrates a deposition process in which the substrate was silicon. The surface of the silicon was exposed to an oxygen plasma in the manner previously described herein for purposes of cleaning the surface and creating hydroxyl availability on the silicon surface. $SiCl_4$ was charged to the process chamber from a $SiCl_4$ vapor reservoir, creating a partial pressure of 4 Torr in the coating process chamber. Within 10 seconds, $H_2O$ vapor was charged to the process chamber from a $H_2O$ vapor reservoir, creating a partial pressure of 10 Torr in the coating process chamber. The total pressure in the coating process chamber was 14 Torr. The substrate temperature and the temperature of the process chamber walls was about 35° C. The substrate was exposed to the mixture of $SiCl_4$ and $H_2O$ for a time period of 10 minutes. The silicon oxide coating thickness obtained was about 30 nm. The coating roughness in RMS was 4.2 nm and Ra was 3.4 nm.

Example Six

Figure 4:
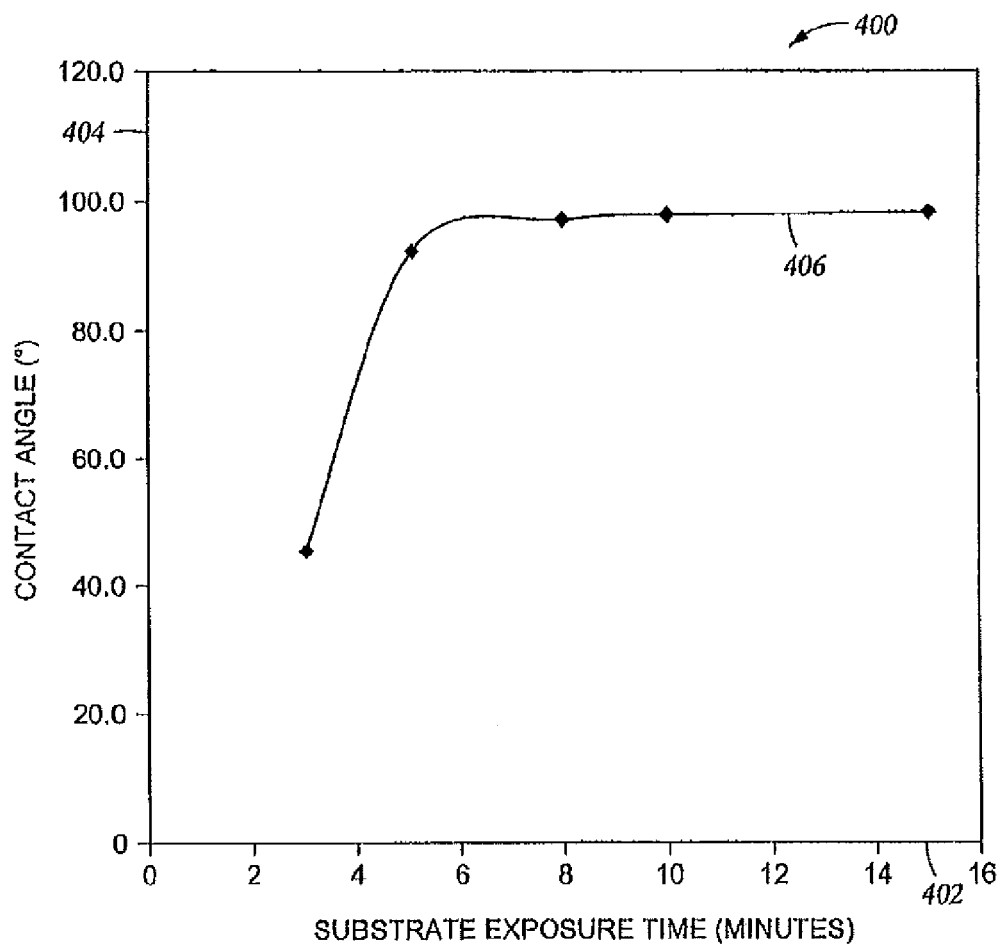
FIG. 4 shows a graph of the water contact angle (proportional to percentage of substrate surface coverage) as a function of time for a coating produced from a dimethyldichlorosilane precursor on the surface of a silicon substrate.

FIG. 4 shows a graph 400 of the dependence of the water contact angle (an indication of hydrophobicity of a surface) as a function of the substrate exposure time for a silicon substrate coated directly with an organo-silane coating generated from a DDMS (dimethyldichlorosilane) precursor. The silicon substrate was cleaned and functionalized to provide surface hydroxyl groups by an oxygen plasma treatment of the kind previously described herein. DDMS was then applied at a partial pressure of 1 Torr, followed within 10 seconds by $H_2O$ applied at a partial pressure of 2 Torr, to produce a total pressure within the process chamber of 3 Torr.

In FIG. 4, graph 400, the substrate exposure period with respect to the DDMS and $H_2O$ precursor combination is shown in minutes on axis 402, with the contact angle shown in degrees on axis 404. Curve 406 illustrates that it is possible to obtain a wide range of hydrophobic surfaces by controlling the process variables in the manner of the present invention. The typical standard deviation of the contact angle was less than 2 degrees across the substrate surface. Both wafer-to wafer and day-to day repeatability of the water contact angle were within the measurement error of ±2° for a series of silicon samples.

Figure 5:
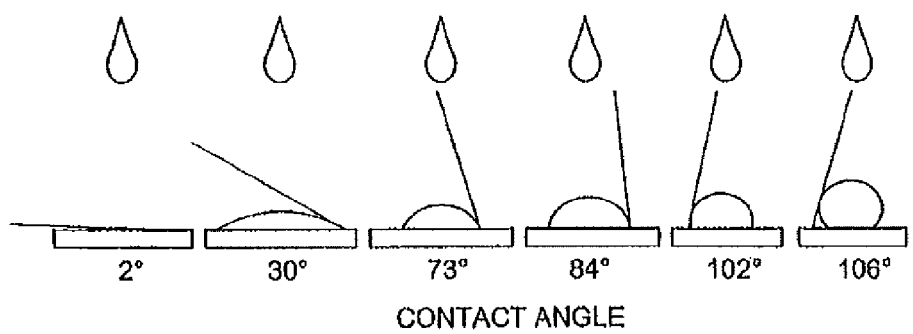
FIG. 5 shows a series of water contact angles measured for a coating surface where the coating was produced from a FOTS precursor on the surface of a silicon substrate. The higher the contact angle, the higher the hydrophobicity of the coating surface.

FIG. 5 illustrates contact angles for a series of surfaces exposed to water, where the surfaces exhibited different hydrophobicity, with an increase in contact angle representing increased hydrophobicity. This data is provided as an illustration to make the contact angle data presented in tables herein more meaningful.

Example Seven

Figure 6A:
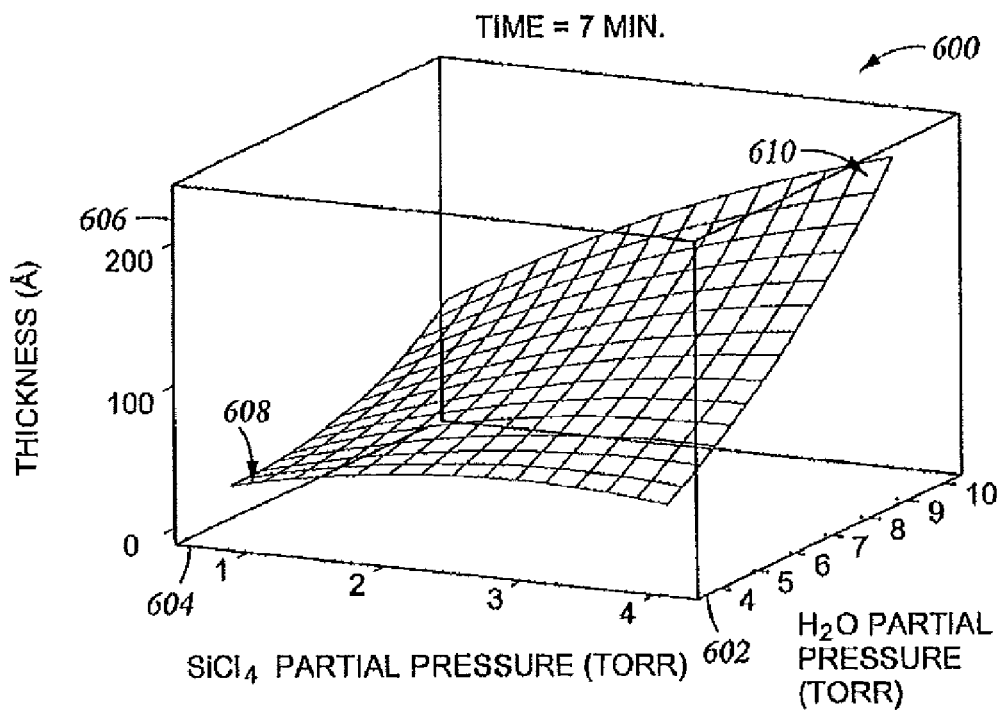
FIG. 6A shows a three dimensional schematic of film thickness of a silicon oxide bonding layer coating deposited on a silicon surface as a function of the partial pressure of silicon tetrachloride and the partial pressure of water vapor present in the process chamber during deposition of the silicon oxide coating, where the time period the silicon substrate was exposed to the coating precursors was four minutes after completion of addition of all precursor materials.
Figure 7A:
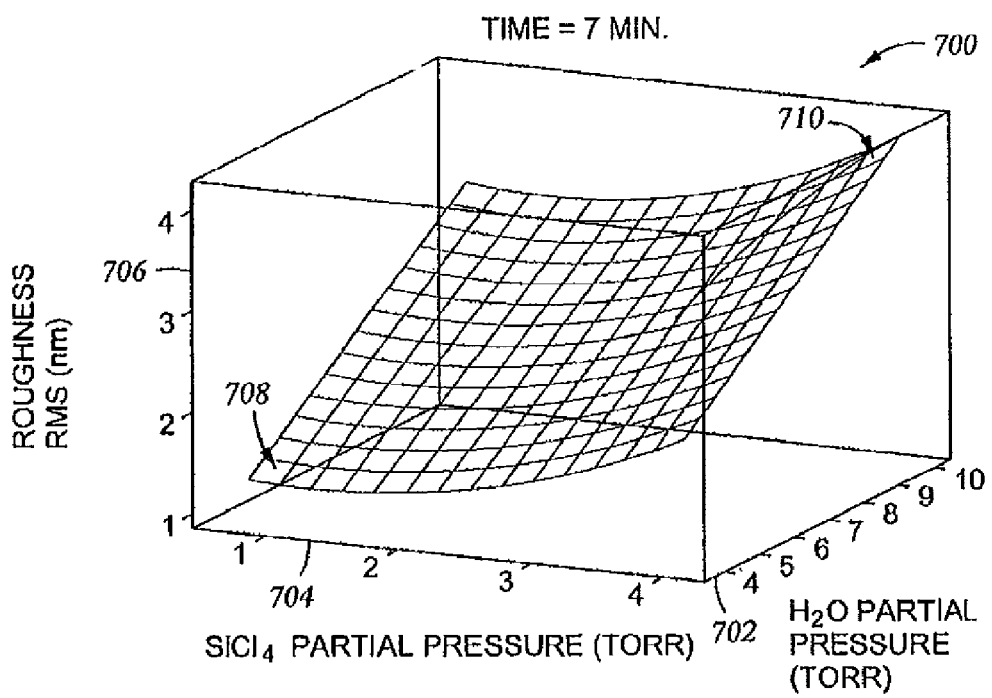
FIG. 7A shows a three dimensional schematic of film roughness in RMS nm of a silicon oxide bonding layer coating deposited on a silicon surface-as a function of the partial pressure of silicon tetrachloride and the partial pressure of water vapor present in the process chamber during deposition of the silicon oxide coating, where the time period the silicon substrate was exposed to the coating precursors was four minutes after completion of addition of all precursor materials.

FIG. 6A shows a three dimensional schematic 600 of film thickness of a silicon oxide bonding layer coating deposited on a silicon surface as a function of the partial pressure of silicon tetrachloride and the partial pressure of water vapor present in the process chamber during deposition of the silicon oxide coating, where the temperature of the substrate and of the coating process chamber walls was about 35° C., and the time period the silicon substrate was exposed to the coating precursors was four minutes after completion of addition of all precursor materials. The precursor $SiCl_4$ vapor was added to the process chamber first, with the precursor $H_2O$ vapor added within 10 seconds thereafter. The partial pressure of the $H_2O$ in the coating process chamber is shown on axis 602, with the partial pressure of the $SiCl_4$ shown on axis 604. The film thickness is shown on axis 606 in Angstroms. The film deposition time after addition of the precursors was 4 minutes. The thinner coatings exhibited a smoother surface, with the RMS roughness of a coating at point 608 on Graph 600 being in the range of 1 nm (10 Å). The thicker coatings exhibited a rougher surface, which was still smooth relative to coatings generally known in the art. At point 610 on Graph 600, the RMS roughness of the coating was in the range of 4 nm (40 Å). FIG. 7A shows a three dimensional schematic 700 of the film roughness in RMS, nm which corresponds with the coated substrate for which the coating thickness is illustrated in FIG. 6A. The partial pressure of the $H_2O$ in the coating process chamber is shown on axis 702, with the partial pressure of the $SiCl_4$ shown on axis 704. The film roughness in RMS, nm is shown on axis 706. The film deposition time after addition of all of the precursors was 7 minutes. As previously mentioned, the thinner coatings exhibited a smoother surface, with the RMS roughness of a coating at point 708 being in the range of 1 nm (10 Å) and the roughness at point 710 being in the range of 4 nm (40 Å).

Figure 6B:
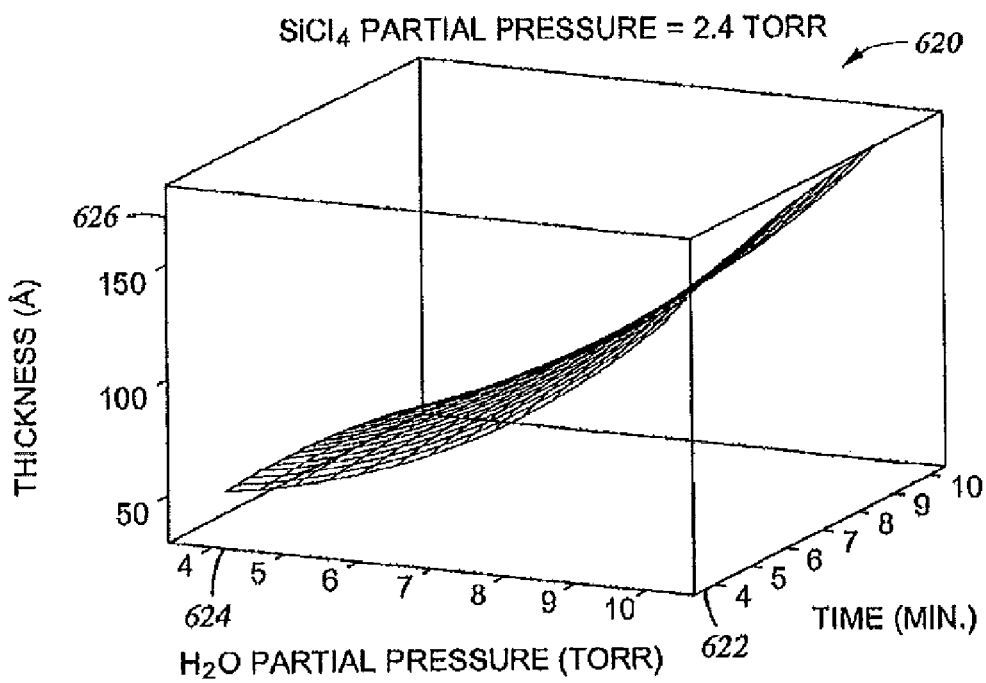
FIG. 6B shows a three dimensional schematic of film thickness of the silicon oxide bonding layer illustrated in FIG. 6A as a function of the water vapor partial pressure and the time period the substrate was exposed to the coating precursors after completion of addition of all precursor materials.

FIG. 6B shows a three dimensional schematic 620 of film thickness of the silicon oxide bonding layer illustrated in FIG. 6A as a function of the water vapor partial pressure and the time period the substrate was exposed to the coating precursors after completion of addition of all precursor materials. The time period of exposure of the substrate is shown on axis 622 in minutes, with the $H_2O$ partial pressure shown on axis 624 in Torr, and the oxide coating thickness shown on axis 626 in Angstroms. The partial pressure of $SiCl_4$ in the silicon oxide coating deposition chamber was 0.8 Torr.

Figure 6C:
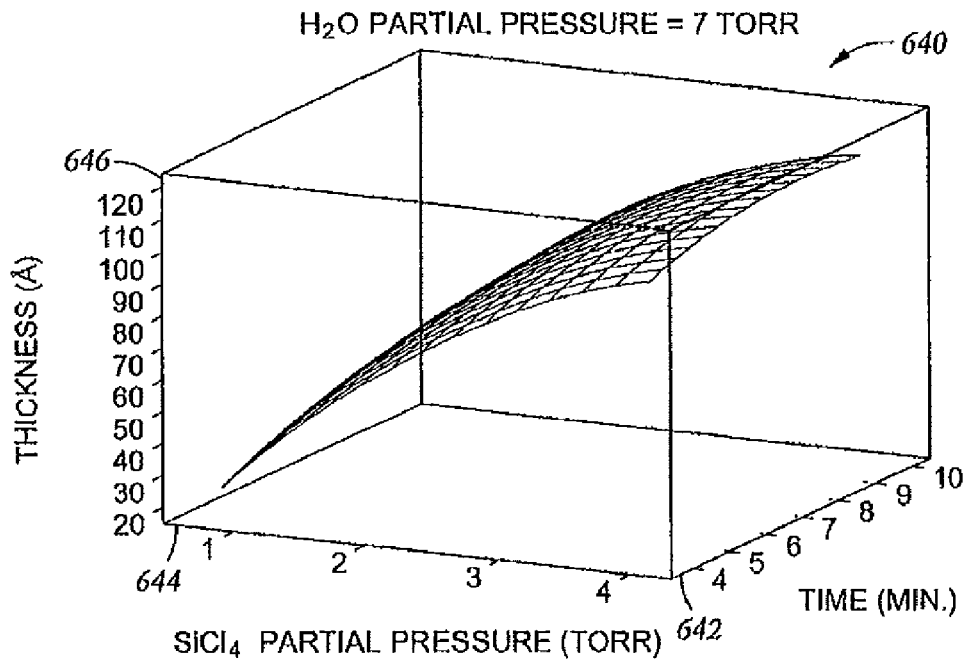
FIG. 6C shows a three dimensional schematic of film thickness of the silicon oxide bonding layer illustrated in FIG. 6A as a function of the silicon tetrachloride partial pressure and the time period the substrate was exposed to the coating precursors after completion of addition of all precursor materials.

FIG. 6C shows a three dimensional schematic 640 of film thickness of the silicon oxide bonding layer illustrated in FIG. 6A as a function of the silicon tetrachloride partial pressure and the time period the substrate was exposed to the coating precursors after completion of addition of all precursor materials. The time period of exposure is shown on axis 642 in minutes, with the $SiCl_4$ partial pressure shown on axis 646 in Torr, and the oxide thickness shown on axis 646 in Angstroms. The $H_2O$ partial pressure in the silicon oxide coating deposition chamber was 4 Torr.

A comparison of FIGS. 6A-6C makes it clear that it is the partial pressure of the $H_2O$ which must be more carefully controlled in order to ensure that the desired coating thickness is obtained.

Figure 7B:
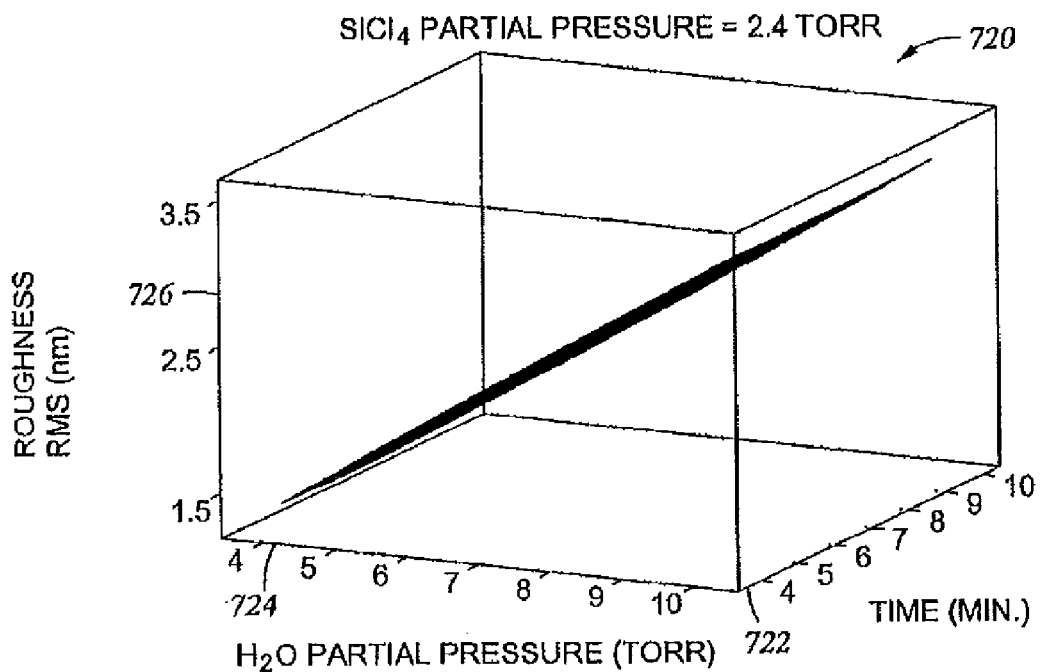
FIG. 7B shows a three dimensional schematic of film roughness in RMS nm of the silicon oxide bonding layer illustrated in FIG. 7A as a function of the water vapor partial pressure and the time period the substrate was exposed to the coating precursors after completion of addition of all precursor materials.

FIG. 7B shows a three dimensional schematic 720 of film roughness of the silicon oxide bonding layer illustrated in FIG. 6B as a function of the water vapor partial pressure and the time period the substrate was exposed to the coating precursors after completion of addition of all precursor materials. The time period of exposure of the substrate is shown on axis 722 in minutes, with the $H_2O$ partial pressure shown on axis 724 in Torr, and the surface roughness of the silicon oxide layer shown on axis 726 in RMS, nm. The partial pressure of the $SiCl_4$ in the silicon oxide coating deposition chamber was 2.4 Torr.

Figure 7C:
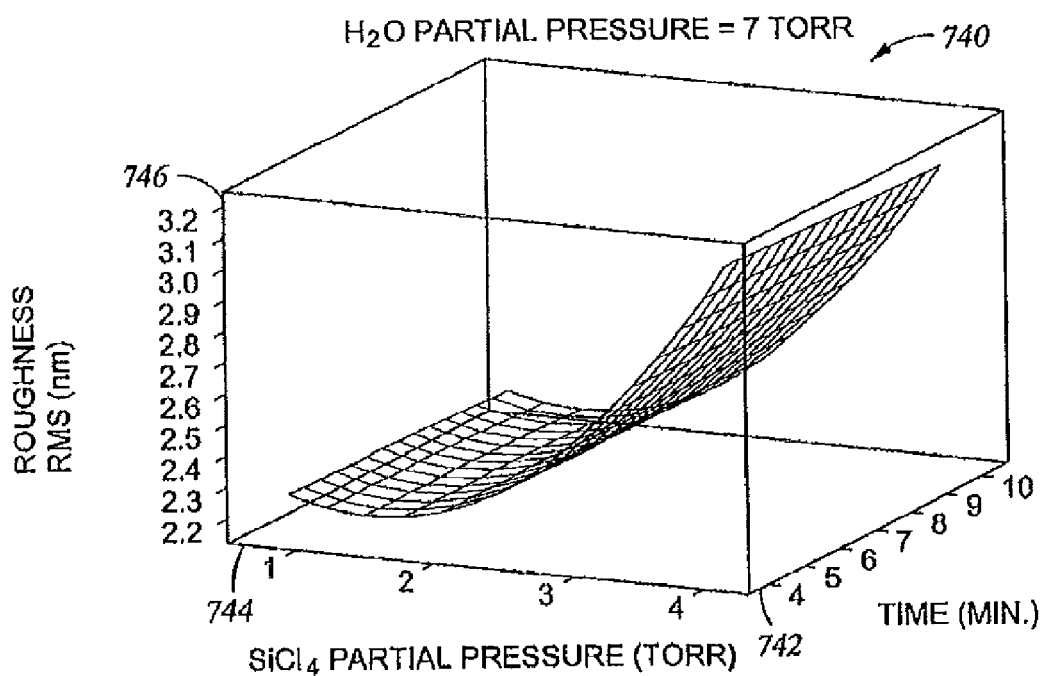
FIG. 7C shows a three dimensional schematic of film roughness in RMS nm of the silicon oxide bonding layer illustrated in FIG. 6A as a function of the silicon tetrachloride partial pressure and the time period the substrate was exposed to the coating precursors after completion of addition of all precursor materials.

FIG. 7C shows a three dimensional schematic 740 of film roughness thickness of the silicon oxide bonding layer illustrated in FIG. 6A as a function of the silicon tetrachloride partial pressure and the time period the substrate was exposed to the coating precursors after completion of addition of all precursor materials. The time period of exposure is shown on axis 642 in minutes, with the $SiCl_4$ partial pressure shown on axis 646 in Torr, and the surface roughness of the silicon oxide layer shown on axis 746 in RMS, nm. The partial pressure of the $H_2O$ in the silicon oxide coating deposition chamber was 7.0 Torr.

A comparison of FIGS. 7A-7C makes it clear that it is the partial pressure of the $H_2O$ which must be more carefully controlled in order to ensure that the desired roughness of the coating surface is obtained.

Figure 8A:
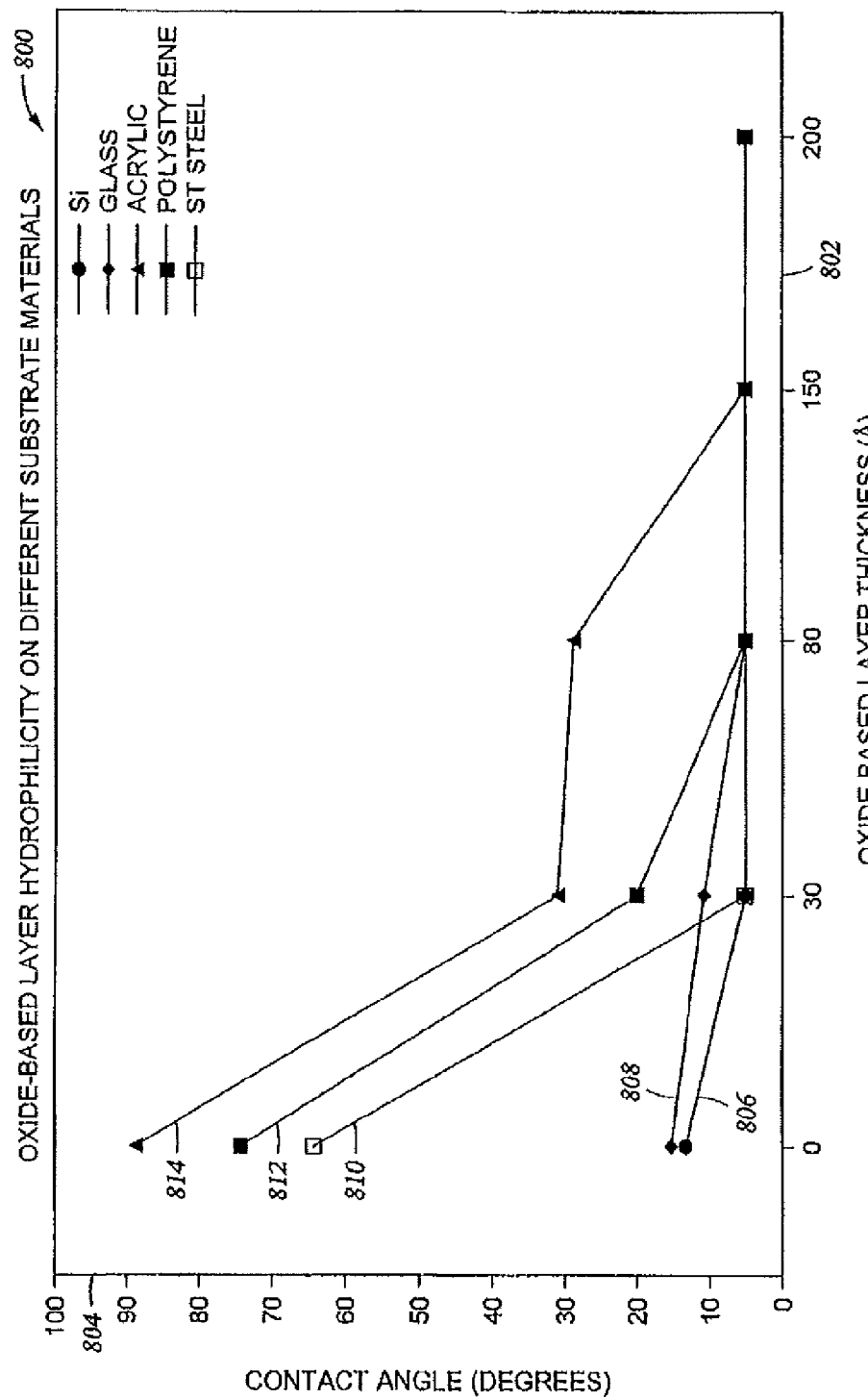
FIG. 8A illustrates the change in hydrophilicity of the surface of the initial substrate as a function of the thickness of an oxide-based bonding layer generated over the initial substrate surface using an oxygen plasma, moisture, and carbon tetrachloride. When the oxide thickness is adequate to provide full coverage of the substrate surface, the contact angle on the surface drops to about 5 degrees or less.

FIG. 8A is a graph 800 which shows the hydrophilicity of an oxide-based layer on different substrate materials, as a function of the thickness of the oxide-based layer. The data presented in FIG. 8A indicates that to obtain full surface coverage by the oxide-based layer, it is necessary to apply a different thickness of oxide-based layer depending on the underlying substrate material.

In particular, the oxide-based layer was a silicon-oxide-based layer prepared in general in the manner described above, with respect to Run No. 4 in Table III, but where the nominal amounts of reactants charged and/or reaction time of the reactants were varied to provide the desired silicon oxide layer thickness, which is specified on axis 802 of FIG. 8A. The graph 800 shows the contact angle for a deionized (DI) water droplet, in degrees, on axis 804, as measured for a given oxide-based layer surface, as a function of the thickness of the oxide-based layer in Angstroms shown on axis 802. Curve 806 illustrates a silicon-oxide-based layer deposited over a single crystal silicon wafer surface. Curve 808 represents a silicon-oxide-based layer deposited over a soda lime glass surface. Curve 810 illustrates a silicon-oxide-based layer deposited over a stainless steel surface. Curve 812 shows a silicon-oxide-based layer deposited over a polystyrene surface. Curve 814 illustrates a silicon-oxide-based layer deposited over an acrylic surface.

Graph 800 shows that a single crystal silicon substrate required only about a 30 .ANG. thick coating of a silicon oxide-based layer to provide a DI water droplet contact angle of about 5 degrees, indicating the maximum hydrophilicity typically obtained using a silicon oxide-based layer. The glass substrate required about 80 Å of the silicon oxide-based layer to provide a contact angle of about 5 degrees. The stainless steel substrate required a silicon oxide-based layer thickness of about 80 Å to provide the contact angle of 5 degrees. The polystyrene substrate required a silicon oxide-based layer thickness of about 80 Å to provide the contact angle of 5 degrees. And, the acrylic substrate required a silicon oxide-based layer thickness of about 150 Å. It should be mentioned that the hydrophilicity indicated in FIG. 8A was measured immediately after completion of the coating process, since the nominal value measured may change during storage.

Figure 8B:
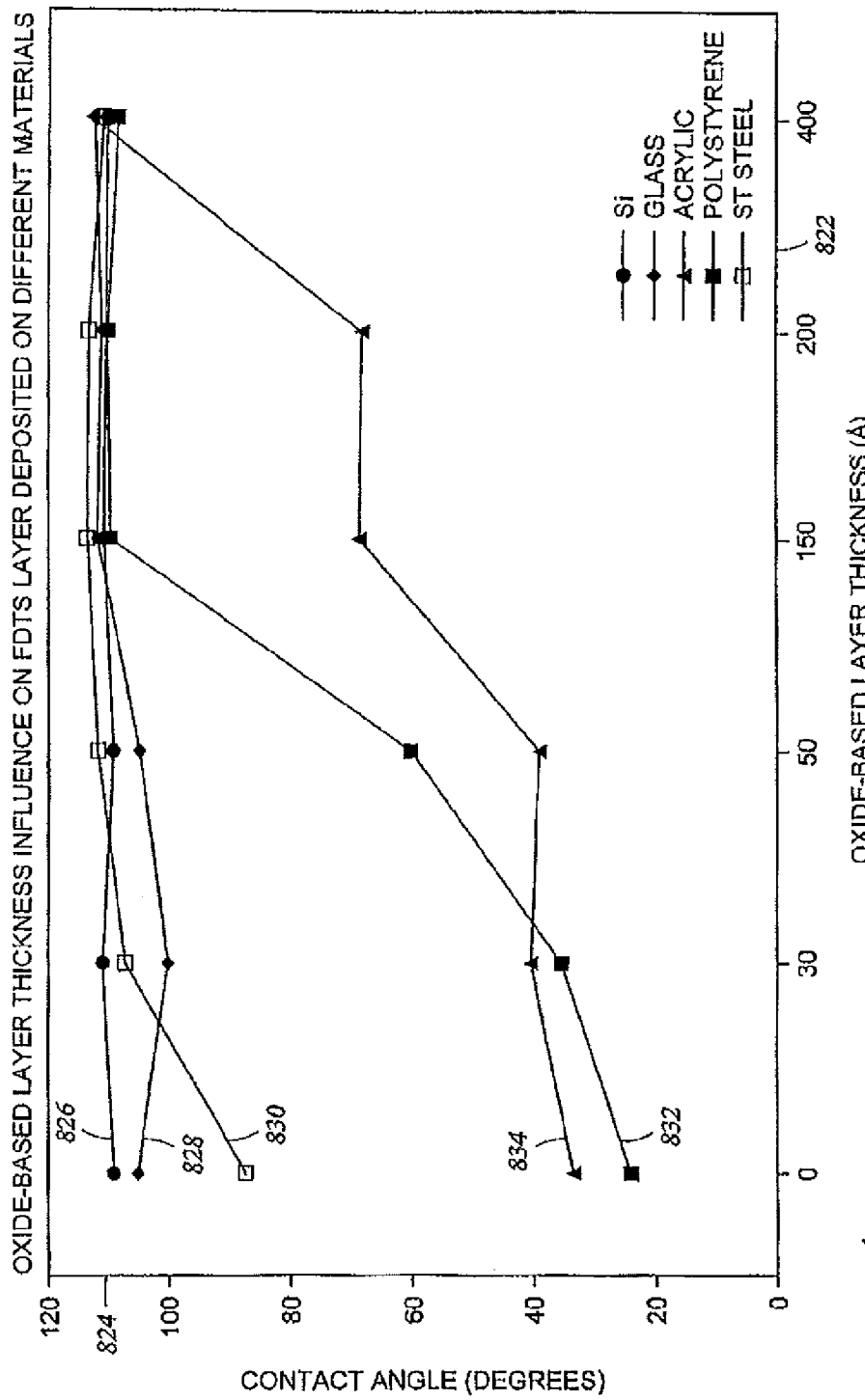
FIG. 8B illustrates the minimum thickness of oxide-based bonding layer which is required to provide adhesion of an organic-based layer, as a function of the initial substrate material, when the organic-based layer is one where the end or the organic-based layer which bonds to the oxide-based bonding layer is a silane and where the end of the organic-based layer which does not bond to the oxide-based bonding layer provides a hydrophobic surface. When the oxide thickness is adequate to provide uniform attachment of the organic-based layer, the contact angle on the substrate surface increases to about 110 degrees or greater.

FIG. 8B shows a graph 820, which illustrates the relationship between the hydrophobicity obtained on the surface of a SAM layer deposited from perfluorodecyltrichlorosilane (FDTS), as a function of the thickness of an oxide-based layer over which the FDTS layer was deposited. The oxide layer was deposited in the manner described above, using tetrachlorosilane precursor, with sufficient moisture that a silicon oxide surface having sufficient hydroxyl groups present to provide a surface contact angle (with a DI water droplet) of 5 degrees was produced.

The oxide-based layer and the organic-based layer generated from an FDTS precursor were deposited as follows: The process chamber was vented and the substrate was loaded into the chamber. Prior to deposition of the oxide-based layer, the surface of the substrate was plasma cleaned to eliminate residual surface contamination and to oxygenate/hydroxylate the substrate. The chamber was pumped down to a pressure in the range of about 30 mTorr or less. The substrate surface was then plasma treated using a low density, non-physically-bombarding plasma which was created externally from a plasma source gas containing oxygen. The plasma was created in an external chamber which is a high efficiency inductively coupled plasma generator, and was fed into the substrate processing chamber. The plasma treatment was in the manner previously described herein, where the processing chamber pressure during plasma treatment was in the range of about 0.5 Torr, the temperature in the processing chamber was about 35° C., and the duration of substrate exposure to the plasma was about 5 minutes.

After plasma treatment, the processing chamber was pumped down to a pressure in the range of about 30 mTorr or less to evacuate remaining oxygen species. Optionally, processing chamber may be purged with nitrogen up to a pressure of about 10 Torr to about 20 Torr and then pumped down to the pressure in the range of about 30 mTorr. An adhering oxide-based layer was then deposited on the substrate surface. The thickness of the oxide-based layer depended on the substrate material, as previously discussed. $SiCl_4$ vapor was injected into the process chamber at a partial pressure to provide a desired nominal oxide-based layer thickness. To produce an oxide-based layer thickness ranging from about 30 Å. to about 400 Å, typically the partial pressure in the process chamber of the $SiCl_4$ vapor ranges from about 0.5 Torr to about 4 Torr, more typically from about 1 Torr to about 3 Torr. Typically, within about 10 seconds of injection of the $SiCl_4$ vapor, water vapor was injected at a specific partial pressure ratio to the $SiCl_4$ to form the adhering silicon-oxide based layer on the substrate. Typically the partial pressure of the water vapor ranges from about 2 Torr to about 8 Torr, and more typically from about 4 Torr to about 6 Torr. (Several volumes of $SiCl_4$ and/or several volumes of water may be injected into the process chamber to achieve the total partial pressures desired, as previously described herein.) The reaction time to produce the oxide layer may range from about 5 minutes to about 15 minutes, depending on the processing temperature, and in the exemplary embodiments described herein the reaction time used was about 10 minutes at about 35° C.

After deposition of the oxide-based layer, the chamber was once again pumped down to a pressure in the range of about 30 mTorr or less. Optionally, the processing chamber may be purged with nitrogen up to a pressure of about 10 Torr to about 20 Torr and then pumped down to the pressure in the range of about 30 mTorr, as previously described. The organic-based layer deposited from an FDTS precursor was then produced by injecting FDTS into the process chamber to provide a partial pressure ranging from about 30 mTorr to about 150 mTorr, more typically ranging from about 100 mTorr to about 300 mTorr. The exemplary embodiments described herein were typically carried out using an FDTS partial pressure of about 150 mTorr. Within about 10 seconds after injection of the FDTS precursor, water vapor was injected into the process chamber to provide a partial pressure of water vapor ranging from about 300 mTorr to about 1000 mTorr, more typically ranging from about 400mTorr to about 800 mTorr. The exemplary embodiments described herein were typically carried out using a water vapor partial pressure of about 600 mTorr. The reaction time for formation of the organic-based layer (a SAM) ranged from about 5 minutes to about 30 minutes, depending on the processing temperature, more typically from about 10 minutes to about 20 minutes, and in the exemplary embodiments described herein the reaction time used was about 15 minutes at about 35° C.

The data presented in FIG. 8B indicates that to obtain the maximum hydrophobicity at the surface of the FDTS-layer, it is not only necessary to have an oxide-based layer thickness which is adequate to cover the substrate surface, but it is also necessary to have a thicker layer in some instances, depending on the substrate underlying the oxide-based layer Since the silicon oxide layer is conformal, it would appear that the increased thickness is not necessary to compensate for roughness, but has a basis in the chemical composition of the substrate. However, as a matter of interest, the initial roughness of the silicon wafer surface was about 0.1 RMS nm, and the initial roughness of the glass surface was about 1-2 RMS nm.

In particular, the oxide-based layer was a silicon-oxide-based layer prepared in the manner described above, with respect to FIG. 8A. The graph 820 shows the contact angle of a DI water droplet, in degrees, on axis 824, as measured for an oxide-based layer surface over different substrates, as a function of the thickness of the oxide-based layer in Angstroms shown on axis 822. Curve 826 illustrates a silicon-oxide-based layer deposited over a single crystal silicon wafer surface described with reference to FIG. 8A. Curve 828 represents a silicon-oxide-based layer deposited over a glass surface as described with reference to FIG. 8A. Curve 830 illustrates a silicon-oxide-based layer deposited over a stainless steel surface, as described with reference to FIG. 8A. Curve 832 shows a silicon-oxide-based layer deposited over a polystyrene surface, as described with reference to FIG. 8A. Curve 834 illustrates a silicon-oxide-based layer deposited over an acrylic surface described with reference to FIG. 8A. The FDTS-generated SAM layer provides an upper surface containing fluorine atoms, which is generally hydrophobic in nature. The maximum contact angle provided by this fluorine-containing upper surface is about 117 degrees. As illustrated in FIG. 8B, this maximum contact angle, indicating an FDTS layer covering the entire substrate surface is only obtained when the underlying oxide-based layer also covers the entire substrate surface at a particular minimum thickness. There appears to be another factor which requires a further increase in the oxide-based layer thickness, over and above the thickness required to fully cover the substrate, with respect to some substrates. It appears this additional increase in oxide-layer thickness is necessary to fully isolate the surface organic-based layer, a self-aligned-monolayer (SAM), from the effects of the underlying substrate. It is important to keep in mind that the thickness of the SAM deposited from the FDTS layer is only about 10 Å to about 20 Å.

Graph 820 shows that a SAM surface layer deposited from FDTS over a single crystal silicon substrate exhibits the maximum contact angle of about 117 degrees when the oxide-based layer overlying the single crystal silicon has a thickness of about 30 Å or greater. The surface layer deposited from FDTS over a glass substrate exhibits the maximum contact angle of about 117 degrees when the oxide-based layer overlying the glass substrate has a thickness of about 150 Å or greater. The surface layer deposited from FDTS over the stainless steel substrate exhibits the maximum contact angle of about 117 degrees when the oxide-based layer overlying the stainless steel substrate has a thickness of between 80 Å and 150 Å or greater. The surface layer deposited from FDTS over the polystyrene substrate exhibits the maximum contact angle when the oxide-based layer overlying the polystyrene substrate has a thickness of 150 Å or greater. The surface layer deposited from FATS over the acrylic substrate exhibits the maximum contact angle when the oxide-based layer overlying the acrylic substrate has a thickness of 400 Å or greater.

Figure 9:
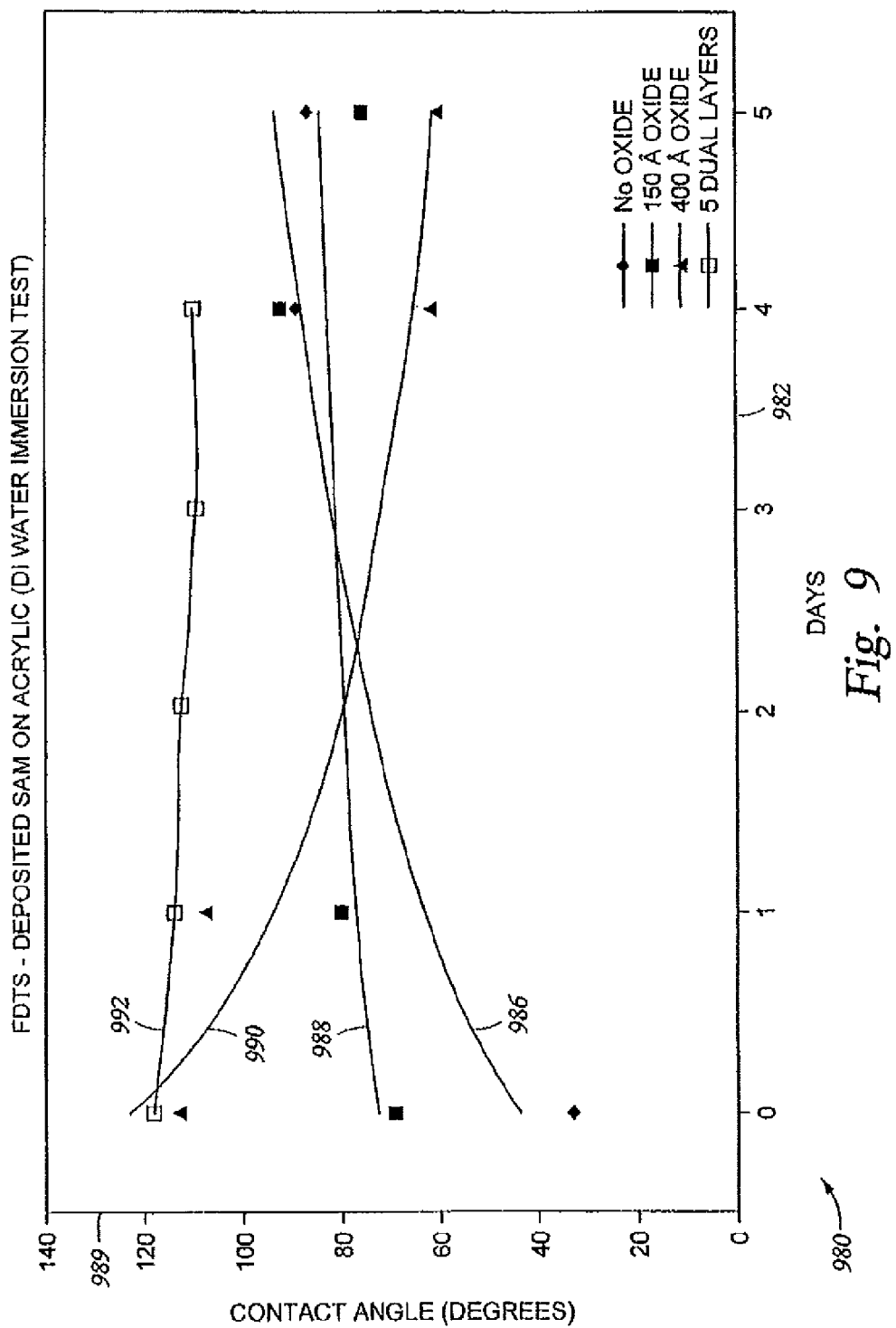
FIG. 9 shows stability in DI water for an organic-based self-aligning monolayer (SAM) generated from perfluorodecyltrichloro-silane (FDTS) applied over an acrylic substrate surface; and, applied over a 150 Å (15 nm) thick oxide-based layer, or applied over a 400 Å (40 nm) thick oxide-based layer, where the initial substrate surface is acrylic. Also shown is the improvement in long-term reliability and performance when a series of five pairs of oxide-based layer/organic-based layer are applied over the acrylic substrate surface.

FIG. 9 illustrates the stability of the hydrophobic surface provided by the SAM surface layer deposited from FDTS, when the coated substrate is immersed in deionized (DI) water for a specified time period. Each test specimen was plasma treated, then coated with oxide and SAM deposited from an FDTS precursor. Each test specimen size was about 1 cm2 on the two major surfaces, and was coated on all sides. Each specimen was immersed into distilled water present in a 6 inch diameter round glass dish, without any means for circulating the water around the sample, and was allowed to stand in the water at atmospheric pressure and at room temperature (about 27° C.). After the time period specified, each specimen was blown dry using a gentle nitrogen gas sparging; there was no baking of the test specimens. After drying, a DI contact angle was measured on the test specimen surface using the contact angle test method previously described herein, which is generally known in the art.

FIG. 9 shows a graph 980 which illustrates the stability of an approximately 15 Å thick layer of a SAM deposited from FDTS over an acrylic substrate without and with various oxide coatings applied over the acrylic substrate surface. Curve 986 shows the contact angle when the SAM was applied directly over the acrylic substrate. Curve 988 shows the contact angle for a test specimen where a 150 Å thick silicon oxide layer was applied over the acrylic substrate surface prior to application of the SAM layer. Curve 990 shows the contact angle for a test specimen where a 400 Å thick silicon oxide layer was applied over the acrylic substrate surface prior to application of the SAM layer. While increasing the thickness of the oxide layer helped to increase the initial hydrophobic properties of the substrate surface (indicating improved bonding of the SAM layer or improved surface coverage by the SAM layer), the structure was not stable, as indicated by the change in contact angle over time. In an effort to provide a more stable structure, we applied a multi-layered structure over the acrylic substrate, with the multilayered structure including a series of five pairs of oxide-based layer/organic-based layer, to provide an organic-based surface layer. Curve 922 shows the stability of the hydrophobic surface layer obtained when this multilayered structure was applied. This indicates that it is possible to provide a stable structure which can withstand extended periods of water immersion by creating the multilayered structure described. The number of pairs (sets) of oxide-based layer/organic-based layer which are required depends on the substrate material. When the substrate material is acrylic, the number of sets of oxide-based layer/organic-based layer which should be used is approximately five sets or more. For other substrate materials, the number of sets of oxide-based layer/organic-based layer may be fewer; however, use of at least two sets of layers helps provide a more mechanically stable structure.

The stability of the deposited SAM organic-based layers can be increased by baking for about one half hour at 110° C., to crosslink the organic-based layers. Baking of a single pair of layers is not adequate to provide the stability which is observed for the multilayered structure, but baking can even further improve the performance of the multilayered structure.

The integrated method for creating a multilayered structure of the kind described above includes: Treatment of the substrate surface to remove contaminants and to provide either —OH or halogen moieties on the substrate surface, typically the contaminants are removed using a low density oxygen plasma, or ozone, or ultra violet (UV) treatment of the substrate surface. The —OH or halogen moieties are commonly provided by deposition of an oxide-based layer in the manner previously described herein. A first SAM layer is then vapor deposited over the oxide-based layer surface. The surface of the first SAM layer is then treated using a low density isotropic oxygen plasma, where the treatment is limited to just the upper surface of the SAM layer, with a goal of activating the surface of the first SAM layer. It is important not to etch away the SAM layer down to the underlying oxide-based layer. By adjusting the oxygen plasma conditions and the time period of treatment, one skilled in the art will be able to activate the first SAM layer surface while leaving the bottom portion of the first SAM layer intact. Typically, the surface treatment is similar to a substrate pretreatment, where the surface is treated with the low density isotropic oxygen plasma for a time period ranging from about 25 seconds to about 60 seconds, and typically for about 30 seconds. In the apparatus described herein the pretreatment is carried out by pumping the process chamber to a pressure ranging from about 15 mTorr to about 20 mTorr, followed by flowing an externally-generated oxygen-based plasma into the chamber at a plasma precursor oxygen flow rate of about 50 sccm to 200 sccm, typically at about 150 sccm in the apparatus described herein, to create about 0.4 Torr in the substrate processing chamber.

After activation of the surface of the first SAM layer using the oxygen-based plasma, a second oxide-based layer is vapor deposited over the first SAM layer. A second SAM layer is then vapor deposited over the second oxide-based layer. The second SAM layer is then plasma treated to activate the surface of the second SAM layer. The process of deposition of oxide-based layer followed by deposition of SAM layer, followed by activation of the SAM surface may be repeated a nominal number of times to produce a multilayered structure which provides the desired mechanical strength and surface properties. Of course there typically is no activation step after deposition of the final surface layer of the multilayered structure, where the surface properties desired are those of the final organic-based layer. It is important to mention that the final organic-based layer may be different from other organic-based layers in the structure, so that the desired mechanical properties for the structure may be obtained, while the surface properties of the final organic-based layer are achieved. The final surface layer is typically a SAM layer, but may also be an oxide-based layer.

As described previously herein, the thickness and roughness of the initial oxide-based layer can be varied over wide ranges by choosing the partial pressure of precursors, the temperature during vapor deposition, and the duration time of the deposition. Subsequent oxide-based layer thicknesses may also be varied, where the roughness of the surface may be adjusted to meet end use requirements. The thickness of an organic-based layer which is applied over the oxide-based layer will depend on the precursor molecular length of the organic-based layer. In the instance where the organic-based layer is a SAM, such as FOTS, for example, the thickness of an individual SAM layer will be in the range of about 15 Å. The thicknesses for a variety of SAM layers are known in the art. Other organic-based layer thicknesses will depend on the polymeric structure which is deposited using polymer vapor deposition techniques. The organic-based layers deposited may be different from each other, and may present hydrophilic or hydrophobic surface properties of varying degrees. In some instances, the organic-based layers may be formed from a mixture of more than one precursor. In some instances, the organic-based layer may be vapor deposited simultaneously with an oxide-based structure to provide cross-linking of organic and inorganic materials and the formation of a dense, essentially pinhole-free structure.

Example Eight

Figure 10A:
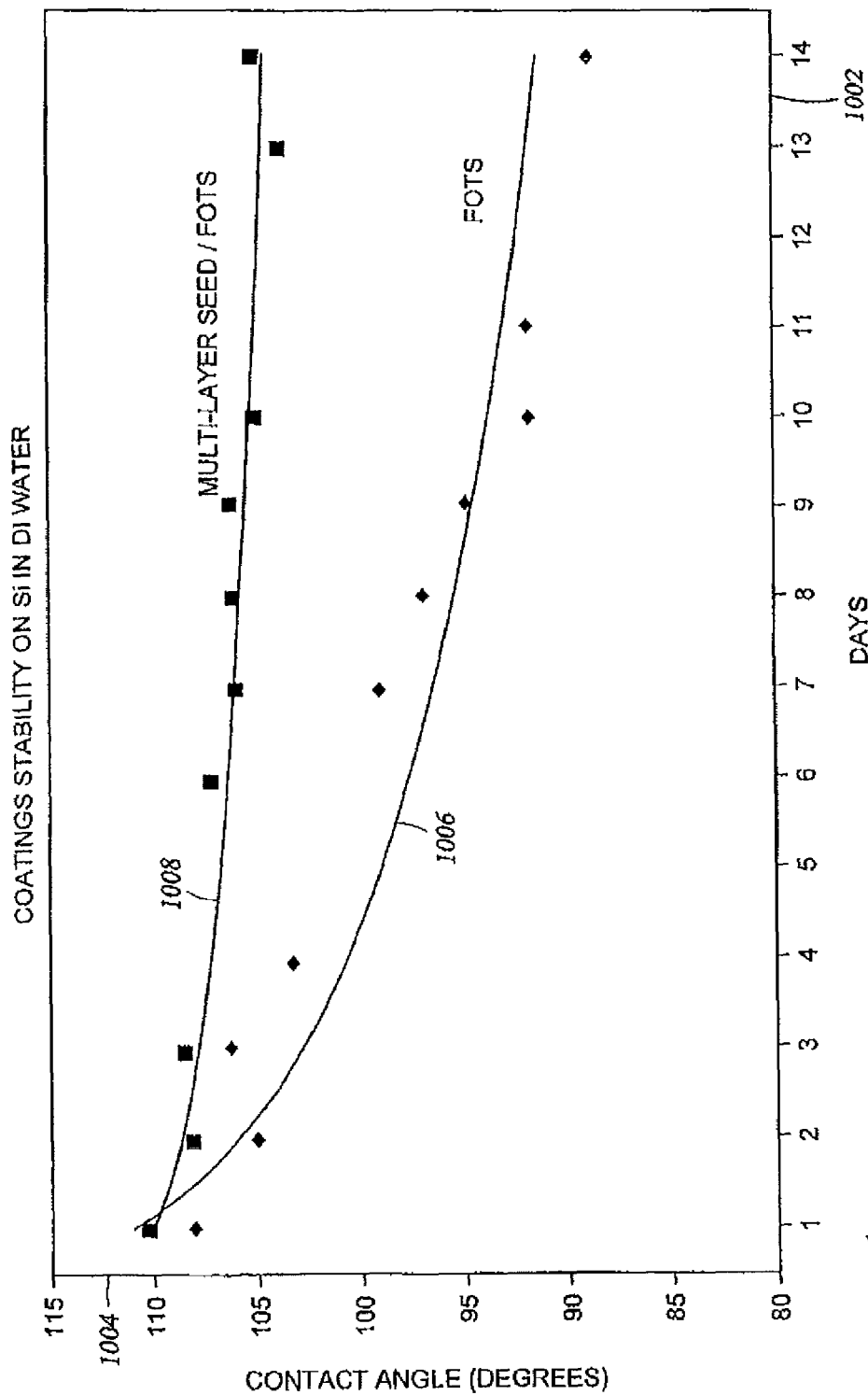
FIG. 10A illustrates the improvement in DI water stability of another multilayered coating, where the organic-based precursor was fluoro-tetrahydrooctyldimethylchlorosilanes (FOTS). The surface stability of a FOTS organic-based layer applied directly over the substrate surface is compared with the surface stability of a FOTS organic-based layer, which is the upper surface layer of a series of alternating layers of oxide-based layer followed by organic based layer.
Figure 10B:
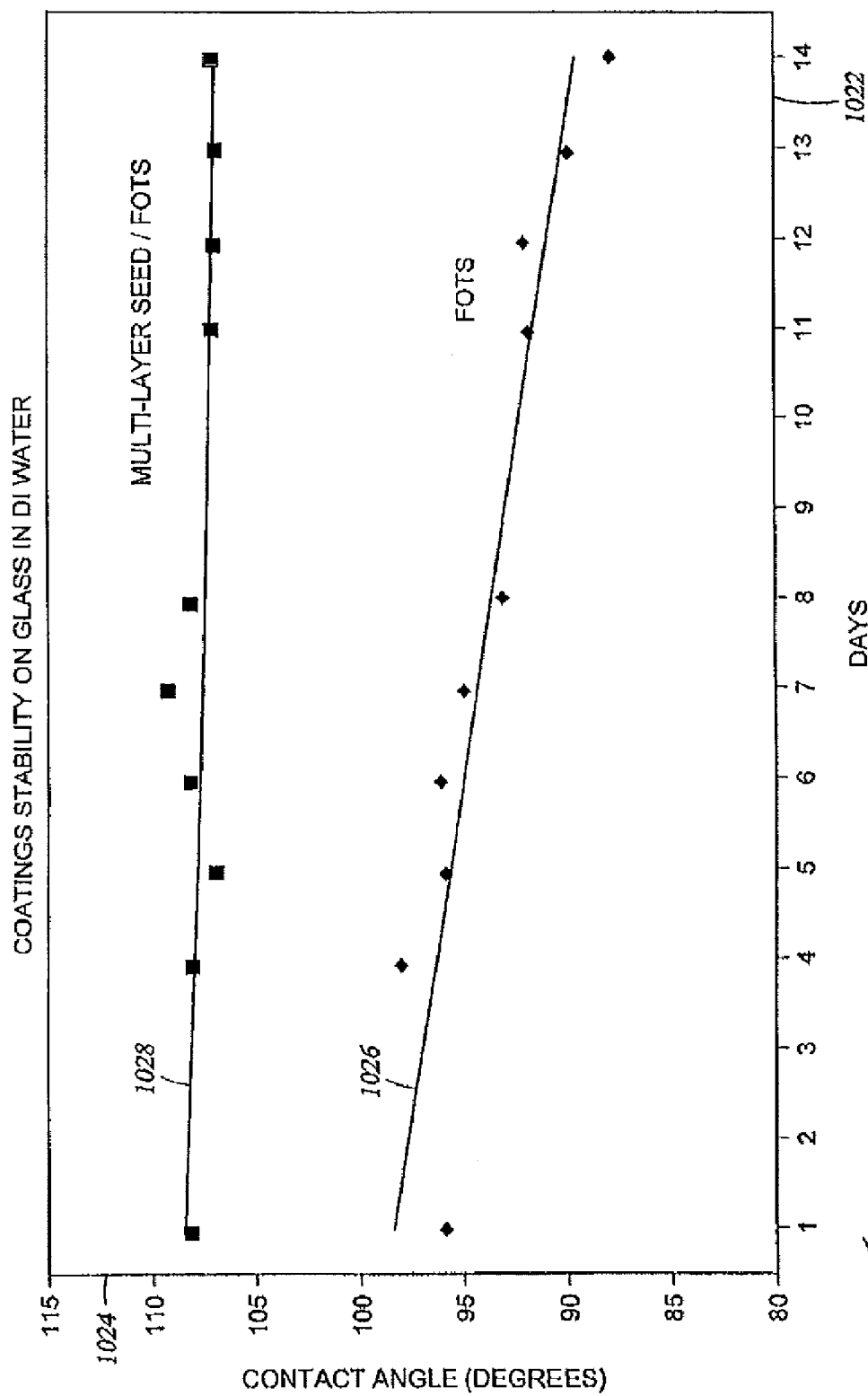
FIG. 10B shows the same kind of comparison as shown in FIG. 10A; however, the substrate is glass.

FIGS. 10A and 10B provide comparative examples which further illustrate the improvement in structure stability and surface properties for a SAM which is deposited from a FOTS precursor over a multilayered structure of the kind described above (with respect to a SAM deposited from FDTS).

FIG. 10A shows a graph 1000 which illustrates the improvement in DI water stability of a SAM when the organic-based precursor was fluoro-tetrahydrooctyldimethylchlorosilanes (FOTS) and the multilayered structure described was present beneath the FOTS based SAM layer. Curve 1008 shows physical property data (contact angle with a DI water droplet) for an approximately 800 Å thick layer of a SAM deposited from FOTS directly upon a single crystal silicon substrate which was oxygen plasma pre-treated in the mariner previously described herein. The DI water droplet contact angle is shown on axis 1004 in degrees; the number of days of immersion of the substrate with overlying oxide and SAM layer in place) is shown on axis 1002 in days. For a silicon substrate (which provides a hydrophilic surface), with the FOTS applied directly over the substrate, the stability of the organic-based SAM layer, in terms of the hygroscopic surface provided, decreases gradually from an initial contact angle of about 108° to a contact angle of less than about 90° after a 14 day time period, as illustrated by curve 1006.

This decrease in contact angle compares with a decrease in contact angle from about 110° to about 105° over the 14 day time period, when the structure is a series of five pairs of silicon oxide/FOTS SAM layers, with a SAM surface layer, as illustrated by curve 1008.

FIG. 10B shows a graph 1020 illustrating stability in DI water for the same FOTS organic-based SAM layer applied directly over the substrate or applied over a series of five pairs of silicon oxide/FOTS SAM layers, when the substrate is soda lime glass. The DI water droplet contact angle is shown on axis 1024 in degrees; the number of days of immersion of the substrate with overlying oxide and SAM layer in place) is shown on axis 1022 in days.

When the FOTS SAM layer was applied directly over the substrate, the stability of the organic-based SAM layer, in terms of the hygroscopic surface provided, decreased gradually from an initial contact angle of about 98° to a contact angle of less than about 88° after a 14 day time period, as illustrated by curve 1026. This compares with a decrease in contact angle from about 108° to about 107° over the 14 day time period, when the structure is a series of five pairs of silicon oxide/POTS SAM layers, as illustrated by curve 1028.

Example Nine

Figure 11B:
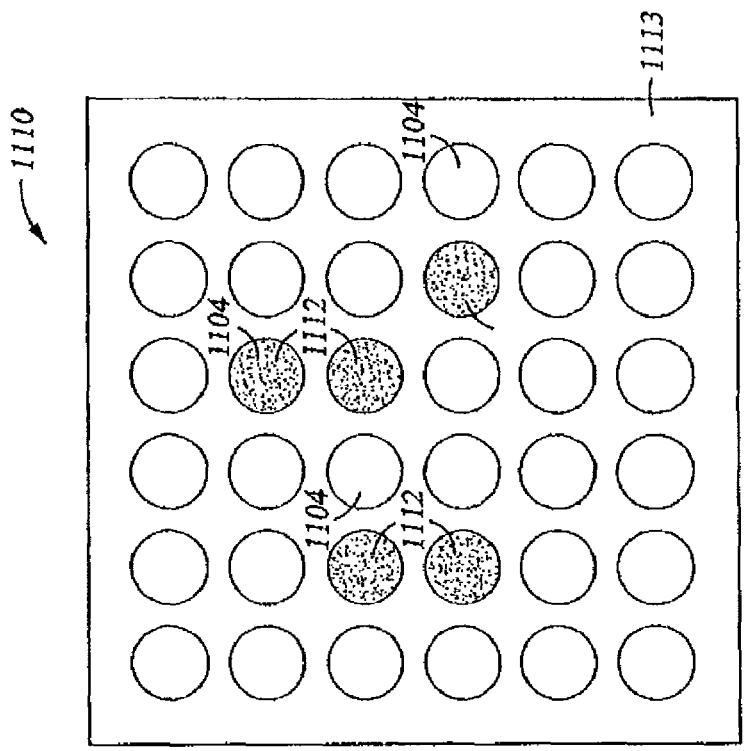
FIG. 11B shows the same 1536-well micro-plate, where a two layer coating having an oxide bonding layer and a monofunctional PEG (mPEG) surface layer renders the hydrophobic micro-plate surface shown in FIG. 11A hydrophilic, so that a fluid sample can more easily enter the well.
Figure 11A:
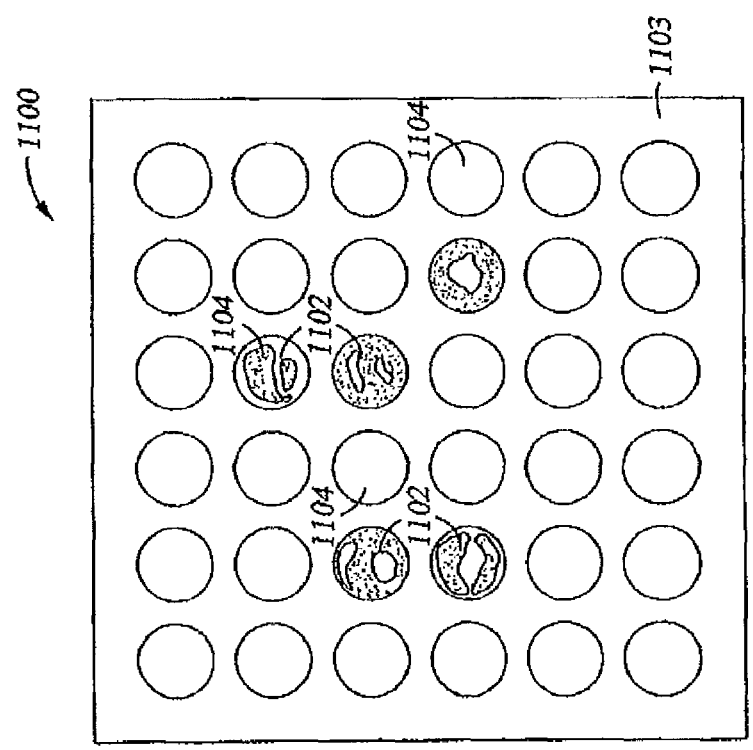
FIG. 11A shows a 1536-well micro-plate, which is typically polystyrene or polypropylene with 1536 wells present in the substrate surface. Each well is about 1.5 to 2.0 mm in diameter and 5.0 min deep. Typical micro-plate well aspect ratios may range from about 1:1 to about 4:1.

FIGS. 11A and 11B show schematic views of the top surfaces of high throughput screening (HTS) micro-plates, where water droplets were applied to small wells in the plates. FIG. 11A illustrates the ability of the water droplet to flow into the wells in the plate with no coating on the polystyrene substrate of the screening plate. FIG. 11B illustrates the ability of the water drop to flow into the wells in the plate when a 150 Å thick oxide layer was applied by molecular vapor deposition (MVD™, Applied MicroStructures, Inc., San Jose, Calif.) over the polystyrene surface, followed by MVD™ of a layer of biocompatible, monofunctional PEG (mPEG) at a thickness of about 20 Å.

In particular, precise control of liquid volume and flow in testing micro-arrays is critical to the accuracy and consistency of analytical results achieved from such testing.

The material to be tested, typically a water-based material, is pipetted (commonly by robot) into very small channels (wells) formed within a screening plate.

For example, a 1536-well screening micro-plate typically measures about 130 mm.times.85 mm×10 mm (L×W×H) and contains 1536 small wells. In a 1536-well screening microplate, a well typically has a volume of about 12 µl. A microplate well normally has a diameter ranging from about 1.0 mm to about 2.0 mm and extends to a depth ranging from about 1.0 mm deep to about 5.0 mm deep. As a result, the aspect ratio (the depth of the well divided by the diameter of the well) of a well ranges from about 0.5:1 to about 5:1. Typically, an aspect ratio ranges from about 2:1 to about 4:1.

Most micro-plates are made of very hydrophobic materials, such as polystyrene or polypropylene, each of which has a water contact angle of around 100°. Water readily beads up on these materials, making it difficult to fill narrow wells formed within micro-plates made from such hydrophobic materials. The difficulty in filling these wells will become more severe in future micro-plates with higher well density.

The droplet size of a droplet of water-based material applied to each well often ranges from about 1 mm to about 3 mm. Allowing for even small amounts of imprecision in application of a droplet of water-based material, it is apparent why a droplet may trap air in the well and sit at the top of the well. This occurred when the polystyrene substrate of the micro-plate 1100 (shown in FIG. 11A) was not prepared by the method of the invention, as illustrated by bubbles 1102 of the water-based material droplets on the upper surface 1103 of micro-plate 1100 at each well 1104.

FIG. 11B shows how the water-based material flowed into the wells in the micro-plate 1110, to provide a relatively flush upper surface 1112 of the water-based material on the upper surface 1113 of micro-plate 1110 at each well 1114.

The droplets of water-based material were comprised of deionized water. The micro-plate polystyrene substrates were at 25° C., and the length of time permitted for the water-based material to flow into the wells was about 2-3 seconds with respect to the test results illustrated above.

The oxide/PEG-coated micro-plates were prepared as follows: The surface of the polystyrene plate was exposed to an oxygen plasma (150 sccm $O_2$ at an RF power of about 200 W in an Applied MicroStructures' MVD™ process chamber) for 5 minutes in order to clean the surface and create hydroxyl availability on the polystyrene surface. $SiCl_4$ was charged to the process chamber front a $SiCl_4$ vapor reservoir, where the $SiCl_4$ vapor pressure in the vapor reservoir was 18 Torr, creating a partial pressure of 2.4 Torr in the coating process chamber. Within 5 seconds, a first volume of $H_2O$ vapor was charged to the process chamber from a $H_2O$ vapor reservoir, where the $H_2O$ vapor pressure in the vapor reservoir was 18 Torr. A total of five chamber volumes of $H_2O$ were charged, creating a partial pressure of 6.0 Torr in the coating process chamber. The total pressure in the coating process chamber was 9 Torr. The substrate temperature and the temperature of the process chamber walls was about 35° C. The substrate was exposed for a time period of about 10 minutes after each $H_2O$ addition. The silicon oxide coating thickness obtained was about 150 Å.

To apply the mPEG coating, MPEG (methoxy(polyethyleneoxy)propyltrimethoxysilane, Gelest P/N SIM 6492.7, MW=450-620, or methoxy(polyethyleneoxy)propyltrichlorosilane, Gelest P/N SIM 6492.66, MW=450-620) was charged to the process chamber from an mPEG vapor reservoir, where the mPEG vapor pressure in the vapor reservoir was about 2 Torr. Four chamber volumes of mPEG were charged, creating a partial pressure of 650 mTorr in the coating process chamber. The substrate was exposed to MPEG vapor each time for a time period of 15 minutes. The substrate temperature and the temperature of the process chamber walls was about 350° C. The MPEG coating thickness obtained was about 20 Å.

The HTS micro-plate embodiment illustrates the use of a hydrophilic coating to draw a water-based substance into wells in an HTS micro plate which is formed from plastic In one embodiment, the interior of the wells has been coated to provide a hydrophilic surface, while the exterior surface of the plate remains hydrophobic because it has not been coated. This may be accomplished using a masking material over the plastic surface exterior of the wells during application of a coating which provides a hydrophilic surface over the interior of the wells. The hydrophobic surface surrounding a well helps force the water-based droplet into the hydrophilic interior of the well, and reduces the possibility of well-to-well contamination of samples being tested.

The above described exemplary embodiments are not intended to limit the scope of the present invention, as one skilled in the art can, in view of the present disclosure expand such embodiments to correspond with the subject matter of the invention claimed below.

All references cited herein are hereby incorporated by reference in their entirety including any references cited therein.

Although the present invention has been described in terms of specific embodiments, changes and modifications can be carried out without departing from the scope of the invention which is intended to be limited only by the scope of the claims.

The invention claimed is:

1. A method for providing an intraocular lens surface with a hydrophilic polymer coating comprising:
   applying at least one hydrophilic polymer coating to at least one surface of said intraocular lens using vapor deposition,
   wherein the vapor deposition comprises the steps of:
   a) exposing a surface of the intraocular lens to an oxygen-comprising plasma in a processing chamber which is at subatmospheric pressure;
   b) subsequently, without exposure of said oxygen-comprising plasma treated surface to ambient conditions which contaminate or react with said plasma treated surface, exposing said surface to a silicon chloride containing vapor in the presence of moisture, to form a hydrophilic silicon oxide layer on said surface; and
   c) subsequently, without exposure of said hydrophilic silicon oxide layer to ambient conditions which contaminate or react with said hydrophilic silicon oxide layer, exposing said silicon oxide layer to a polyethylene glycol polymer having a plurality of monomers to form a layer selected from the group consisting of a monolayer, a self-aligned monolayer, and a polymerized cross-linked layer, wherein of the monomers have a structure of Formula 1:

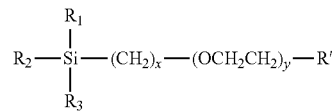

Formula 1 wherein $R_1$, $R_2$ and $R_3$ can be, individually a chlorine or a methoxy group;
x is 3;
y is an integer from 6 to 9; and
R' is a methoxy.

2. The method according to claim 1 wherein $R_1$, $R_2$ and $R_3$ all comprise methoxy groups.

3. The method according to claim 1 wherein said monomer has the structure of Formula 2:

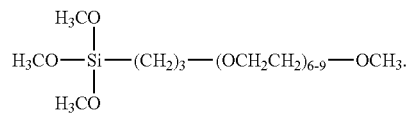

Formula 2

* * * * *